United States Patent [19]

Ellis et al.

[11] Patent Number: 5,023,255
[45] Date of Patent: Jun. 11, 1991

[54] CHEMICAL COMPOUNDS

[75] Inventors: Frank Ellis, Luton; Alan Naylor, Royston; Christopher J. Wallis, Royston; Ian Waterhouse, Royston, all of England

[73] Assignee: Glaxo Group Limited, England

[21] Appl. No.: 493,250

[22] Filed: Mar. 14, 1990

[30] Foreign Application Priority Data

Mar. 15, 1989 [GB] United Kingdom ............... 8905914
Oct. 26, 1989 [GB] United Kingdom ............... 8924135
Oct. 26, 1989 [GB] United Kingdom ............... 8924138

[51] Int. Cl.$^5$ .................... C07D 253/06; A61K 31/53
[52] U.S. Cl. ....................................... 514/242; 544/182
[58] Field of Search ..................... 544/182; 514/242

[56] References Cited

U.S. PATENT DOCUMENTS 4,767,760  8/1988  Boeckx ............................... 514/242

FOREIGN PATENT DOCUMENTS 058534A  8/1982  European Pat. Off. .
154885   9/1985  European Pat. Off. .
215354   3/1987  European Pat. Off. .
299449   1/1989  European Pat. Off. .
3531919  3/1988  Fed. Rep. of Germany .

OTHER PUBLICATIONS

Minlibaeva et al., Chemical Abstracts, vol. 88, entry 152571s, (1978).
Frerichs et al., Arch. Pharm., vol. 237, pp. 346–358, (1899).
Busch, Chem. Ber., 1903, 3877–90, p. 3884.
Minlibaeva et al., Org. Khim, 1976, 99–102 with translation.
G. Heberlein, Annalen, 1898, 301 58–69.

*Primary Examiner*—John M. Ford
*Attorney, Agent, or Firm*—Bacon & Thomas

[57] ABSTRACT

Triazine derivatives of formula (I)

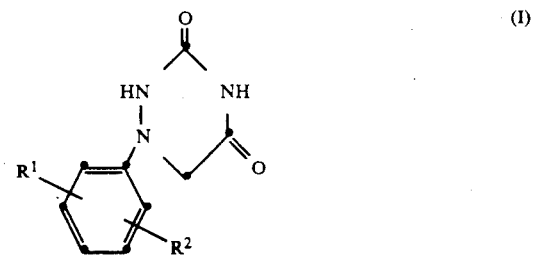

or salts thereof, wherein $R^1$ represents a halogen atom or a group selected from hydroxy; $C_{1-8}$ alkyl $C_{1-6}$ alkoxy; $C_{1-3}$ alkoxy $C_{1-3}$ alkoxy; phenoxy or phenyl $C_{1-3}$ alkoxy, wherein the phenyl group is optionally substituted by a halogen atom or a group selected from $C_{1-3}$ alkyl, $C_{1-3}$ alkoxy, or hydroxy; fluoro $C_{1-3}$ alkyl; cyano; $-CO_2R^3$, wherein $R^3$ represents a hydrogen atom or a $C_{1-4}$ alkyl group; $-CONR^4R^5$, wherein $R^4$ and $R^5$ each independently represents a hydrogen atom or a $C_{1-4}$ alkyl group, or, together with the nitrogen atom to which they are attached, form a saturated 5- to 7- membered ring, which ring optionally contains one or more atoms selected from an oxygen or a sulphur atom, or a group selected from $-NH-$ or $-N(CH_3)-$; and $R^2$ represents a hydrogen or halogen atom, or a group selected from hydroxy, $C_{1-6}$ alkyl or $C_{1-6}$ alkoxy;

are inhibitors of the enzyme 5-lipoxygenase.

Processes for preparing the triazine derivatives of formula (I) and compositions containing them are also described.

22 Claims, No Drawings

CHEMICAL COMPOUNDS

This invention relates to heterocyclic compounds, to processes for their preparation, to pharmaceutical compositions containing them and to their use in medicine. In particular, the invention relates to compounds which act as inhibitors of the enzyme 5-lipoxygenase.

The enzyme 5-lipoxygenase catalyses the first reaction in the biosynthesis of potent biological mediators, for example the leukotrienes ($LTB_4$, $LTC_4$, $LTD_4$, $LTE_4$), from arachidonic acid. The leukotrienes $LTC_4$, $LTD_4$ and $LTE_4$ and other 5-lipoxygenase products are widely believed to be the prime mediators in the pathogenesis of allergic asthma. The leukotriene $LTB_4$ is believed to be a mediator in the pathogenesis of inflammation. Thus compounds which inhibit the enzyme 5-lipoxygenase should reduce the production of these potent biological mediators and hence be useful for the treatment of diseases arising from the over-production of these mediators. Such diseases include respiratory diseases of the airways such as asthma, bronchitis, adult respiratory distress syndrome, allergic rhinitis and sarcoidosis of the lung; inflammation of the gastrointestinal tract including gastritis, oesophagitis, duodenitis, inflammatory bowel disease (such as ulcerative colitis), irritable bowel syndrome, peptic ulceration, Crohn's disease and coeliac disease; inflammation of the joints including rheumatoid arthritis, rheumatoid spondylitis, osteoarthritis and gouty arthritis; diseases of the skin including psoriasis, eczema, contact dermatitis and atopic dermatitis; ischaemia of major organs including, brain, liver and kidney; ischaemic heart disease including angina and myocardial infarction and cardiovascular disorders such as peripheral vascular disease and cerebrovascular disease. In addition, compounds which inhibit the enzyme 5-lipoxygenase may be useful for suppressing tissue rejection following transplant surgery, in the treatment of endotoxin shock and benign prostatic hypertrophy and as cytoprotective agents.

Arachidonic acid is also an essential element in the biosynthesis of a number of other important mediators in the human body. It is therefore desirable that any 5-lipoxygenase inhibitor should have little or no effect on the biosynthesis of other mediators from arachidonic acid.

We have now found a novel group of heterocyclic compounds which are potent and selective inhibitors of the enzyme 5-lipoxygenase.

Thus in one aspect the invention provides a triazine derivative of formula (I):

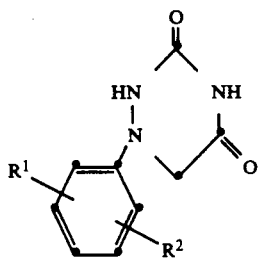

or a salt thereof, in particular a physiologically acceptable salt thereof,
wherein
$R^1$ represents a halogen atom, or a group selected from hydroxy; $C_{1-8}$alkyl; $C_{1-6}$ alkoxy; $C_{1-3}$ alkoxy $C_{1-3}$ alkoxy; phenoxy or a phenyl-$C_{1-3}$ alkoxy, wherein the phenyl group is unsubstituted or substituted by a halogen atom or a $C_{1-3}$ alkyl, $C_{1-3}$ alkoxy or hydroxy group; fluoro $C_{1-3}$ alkyl; cyano; $CO_2R^3$, wherein $R^3$ represents a hydrogen atom or a $C_{1-4}$ alkyl group; —$CONR^4R^5$, wherein $R^4$ and $R^5$ each independently represents a hydrogen atom or a $C_{1-4}$ alkyl group, or together with the nitrogen atom to which they are attached form a saturated 5- to 7-membered ring, which ring optionally contains one or more atoms selected from an oxygen or a sulphur atom, or a group —NH— or —N(CH$_3$)—; and $R^2$ represents a hydrogen or a halogen atom, or a hydroxy, $C_{1-6}$ alkyl or $C_{1-6}$ alkoxy group.

Referring to formula (I), a halogen atom may be a fluorine, chlorine, bromine or iodine atom. An alkyl group (as such or as part of a group) may be a straight or branched chain alkyl group. A $C_{1-6}$alkyl group may be, a methyl, ethyl, propyl, butyl, pentyl or hexyl group. A $C_{1-8}$ alkyl group may additionally be a heptyl or an octyl group. A $C_{1-6}$alkoxy group may be, for example, a methoxy, ethoxy, propoxy, butoxy, pentoxy or hexyloxy group. A phenyl $C_{1-3}$ alkoxy group may be, for example, a benzyloxy, a phenylethoxy or a phenylpropoxy group, especially a benzyloxy group.

The substituent(s) on the phenyl ring may be at the 2-, 3-, 4-, 5- or 6-position(s). Preferably, however, $R^1$ is a 3- or 4-phenyl substituent.

Particular examples of a disubstituted phenyl group include phenyl substituted by two alkyl (e.g. methyl) groups or by two halogen (e.g. fluorine) atoms or by an alkyl group and a halogen atom.

In preferred embodiments of the present invention, $R^1$ represents a halogen atom or a group selected from $C_{1-8}$ alkyl; $C_{1-6}$ alkoxy; $C_{1-3}$ alkoxy $C_{1-3}$ alkoxy; phenoxy or a phenyl $C_{1-3}$alkoxy, wherein the phenyl group is unsubstituted or substituted by a halogen atom or a $C_{1-3}$ alkyl, $C_{1-3}$ alkoxy or hydroxy group; fluoro $C_{1-3}$ alkyl. Conveniently the fluoro $C_{1-3}$ alkyl group is trifluoromethyl. In a preferred embodiment of the present invention, $R^1$ is a phenyl $C_{1-3}$ alkoxy group. In particularly preferred embodiments of the present invention, $R^1$ represents a halogen (especially a fluorine) atom or a $C_{1-8}$ alkyl especially a $C_{1-3}$ alkyl, most especially a methyl or ethyl, group.

Preferably, $R^2$ represents a halogen (especially fluorine), a $C_{1-6}$ alkyl (especially methyl) group or, which is particularly preferred, a hydrogen atom.

A particularly preferred compound according to the invention is dihydro-1-(3-methylphenyl)-1,2,4-triazine-3,5-(2H,4H)-dione; or a physiologically acceptable salt thereof.

Another preferred compound according to the invention is dihydro-1-(3-ethylphenyl)-1,2,4-triazine-3,5-(2H,4H)-dione; or a physiologically acceptable salt thereof.

Another preferred compound according to the invention is dihydro-1-(3-n-propylphenyl)-1,2,4-triazine-3,5-(2H,4H)-dione or a physiologically acceptable salt thereof.

Another preferred compound according to the invention is dihydro-1-(3-fluorophenyl)-1,2,4-triazine-3,5-(2H,4H) dione; or a physiologically acceptable salt thereof.

Another preferred compound according to the invention is dihydro-1-(4-fluorophenyl)-1,2,4-triazine-3,5-

(2H,4H)-dione; or a physiologically acceptable salt thereof.

Another preferred compound according to the invention is dihydro-1-(3-chlorophenyl)-1,2,4-triazine-3,5-(2H,4H)-dione; or a physiologically acceptable salt thereof.

Another preferred compound according to the invention is dihydro-1-(3-bromophenyl)-1,2,4-triazine-3,5-(2H,4H)-dione; or a physiologically acceptable salt thereof.

Another preferred compound according to the invention is dihydro-1-(3,5-difluorophenyl)-1,2,4-triazine-3,5-(2H,4H)-dione; or a physiologically acceptable salt thereof.

Another preferred compound according to the invention is dihydro-1-(3-methoxyphenyl)-1,2,4-triazine-3,5-(2H,4H)-dione; or a physiologically acceptable salt thereof.

Another preferred compound according to the invention is dihydro-1-[(3-(4-fluorophenylmethoxy)phenyl]-1,2,4-triazine-3,5-(2H,4H)-dione; or a physiologically acceptable salt thereof.

Suitable physiologically acceptable salts of the compounds of formula (I) include acid addition salts formed with organic or inorganic acids, for example hydrochlorides, hydrobromides, sulphates, methanesulphonates, phosphates, citrates, fumarates and maleates. The compounds of formula (I) may also form salts with suitable bases. Examples of such salts are alkali metal (e.g. sodium and potassium) salts.

All optical isomers of the compounds of formula (I) and their mixtures including racemic mixtures thereof are embraced by the invention. All geometric (cis-trans) isomers of the compounds of formula (I) and their mixtures are embraced by the invention. Solvates of the compounds of formula (I) are also embraced by the invention.

The selective 5-lipoxygenase inhibitory action of the compounds of the invention is readily demonstrated using human white blood cells. Thus in tests with human white blood cells stimulated with the compound A 23187 (G. Hansson and O. Radmark, FEBS Letters 1980, 122(1), 87), the compounds of the invention inhibit the synthesis of the leukotrienes $LTC_4$ and $LTD_4$ at concentrations which have little or no effect on the biosynthesis of other mediators from arachidonic acid.

Compounds of formula (I) are thus useful for the treatment of disease states in which the leukotrienes ($LTB_4$, $LTC_4$, $LTD_4$ and $LTE_4$) and other 5-lipoxygenase products are mediators.

Accordingly the invention provides a method of treatment for the relief or prevention of diseases in which leukotrienes and other 5-lipoxygenase products are mediators, which comprises administering to a human or animal subject in need of such treatment an effective amount of a triazine derivative of formula (I) or a physiologically acceptable salt thereof.

It will be appreciated that compounds of the invention will primarily be of use in the alleviation of established symptoms, but prophylaxis is not excluded.

According to another aspect, the invention provides a triazine derivative of formula (I) above or a physiologically acceptable salt thereof for use as an active therapeutic substance, especially in the relief or prevention of diseases in which leukotrienes or other 5-lipoxygenase products are mediators.

According to yet another aspect, the invention provides a pharmaceutical composition which comprises a triazine derivative of formula (I) or a physiologically acceptable salt thereof, formulated for administration by any convenient route, for use in human or veterinary medicine. Such compositions may be formulated in conventional manner using one or more physiologically acceptable carriers and/or excipients.

Thus the compounds of formula (I) may be formulated for oral, buccal, parenteral, topical or rectal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

For topical administration the pharmaceutical composition may take the form of ointments, lotions or creams formulated in a conventional manner, with for example an aqueous or oily base, generally with the addition of suitable thickening agents and/or solvents. For nasal applications, the composition may take the form of a spray, formulated for example as an aqueous solution or suspension or as an aerosol with the use of a suitable propellant.

The compounds of formula (I) may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in a powder form for constitution with a suitable vehicle, e.g. sterile pyrogen-free water, before use.

The compounds of formula (I) may also be formulated in rectal compositions such as suppositories or retention enemas, e.g. containing conventional suppository bases such as cocoa butter or other glycerides.

In addition to the formulations described previously, the compound may also be formulated as a depot preparation. Such long acting formulations may be administered by implantation (for example subcutaneously, transcutaneously or intramuscularly) or by intramuscular injection. Thus, for example, the compounds of formula (I) may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds for use according to the present invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of formula (I) and a suitable powder base such as lactose or starch.

The compositions may, if desired, be presented in a pack or dispenser device which may contain one or more unit dosage forms containing the active ingredient. The pack may for example comprise a metal or plastic foil, such as a blister pack. The pack or dispenser device may be accompanied by instructions for administration.

A proposed daily dose of the compound of the invention for administration to man (of approximately 70 kg body weight) is 1 mg to 2 g, which may be administered, for example, 1 to 4 times per day.

The precise dose will depend on the condition being treated, the route of administration, and the age and the body weight of the patient being treated.

Thus, for example, a suitable daily dose for oral administration is 100 mg to 2 g. For administration by inhalation or insufflation, a preferred dosage unit is 1 to 100 mg, more preferably 1 to 50 mg, which may be given 1 to 4 times daily.

In yet a further aspect the invention also provides for the use of a triazine derivative of formula (I) or a physiologically acceptable salt thereof for the manufacture of a medicament for the relief or prevention of diseases in which leukotrienes or other 5-lipoxygenase products are mediators.

The compounds of formula (I) and physiologically acceptable salts thereof may be prepared by the general methods outlined hereinafter. In the following description, the groups $R^1$ and $R^2$ are as defined for compounds of formula (I).

According to a first general process (A), a triazine derivative of formula (I) may be prepared by cyclising a compound of formula (II):

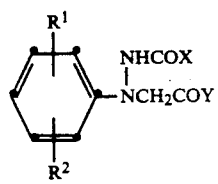

wherein X and Y each represent $NH_2$ or a leaving group, such as a halogen atom or an imidazolide group or $—OR^6$ (wherein $R^6$ represents a lower ($C_{1-4}$) alkyl (e.g. methyl) group, $C_{1-4}$ acyl (e.g. acetyl), $C_{1-4}$ alkoxycarbonyl (e.g. methoxycarbonyl) or $(R^7O)_2$ PO, wherein $R^7$ represents a $C_{1-4}$ alkyl or a phenyl group; provided that when X represents a leaving group, Y represents $NH_2$ and when X represents $NH_2$, Y represents a leaving group.

The cyclisation may be effected preferably using a base such as an alkali metal alkoxide (e.g. sodium methoxide or potassium t-butoxide) or an alkali metal hydroxide (e.g. sodium hydroxide), in a solvent such as an alcohol (e.g. methanol) or a ketone (e.g. methyl isobutyl ketone) conveniently at room temperature. Alternatively, the cyclisation may be carried out using an alkali metal hydride (e.g. sodium hydride) or a tetraalkylammonium fluoride, e.g. tetrabutylamonium fluoride, in an inert solvent such as tetrahydrofuran, conveniently at room temperature.

According to particular embodiments of general process (A), a triazine derivative of formula (I) may be prepared directly by the reaction of a compound of formula (III):

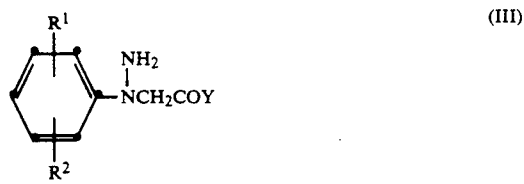

wherein Y represents a suitable leaving group, with an alkali metal, e.g. sodium, cyanate and trifluoroacetic acid in a solvent such as toluene and conveniently at room temperature, followed by cyclisation as described above.

Alternatively, a compound of formula (I) may be prepared directly by the reaction of a compound of formula (II), wherein X represents $NH_2$ and Y represents OH, with diphenyl phosphonic acid azide [$(PhO)_2$ $P(O)N_3$].

Alternatively, a compound of formula (I) may be prepared directly by the reaction of a compound of formula (III), wherein Y represents $NH_2$, with N, N'-carbonyldiimidazole (CDI) or phosgene, followed by cyclisation as described above.

In these particular embodiments, compounds of formula (II) wherein one of X and Y represents a leaving group and the other represents $NH_2$ may be isolated as intermediates.

Compounds of formula (II) wherein one of X and Y represents a leaving group and the other represents $NH_2$ are novel compounds and constitute a further aspect of this invention.

Compounds of formula (III) wherein Y represents a leaving group are also novel compounds and constitute a yet further aspect of this invention.

Compounds of formula (II) in which Y represents a leaving group may be prepared, for example, by the reaction of a compound of formula (III) with sodium cyanate and trifluoroacetic acid. The reaction may conveniently be effected in a solvent such as toluene and at room temperature.

Compounds of formula (II), in which Y represents a leaving group may also be prepared, for example, by reaction of a compound of formula (IV):

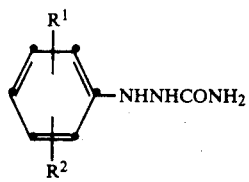 (IV)

with a compound of formula (V)

LCH₂COY      (V)

wherein L represents a leaving group, preferably a halogen atom (e.g. a chlorine or a bromine atom), and Y is a suitable leaving group as defined previously, in the presence of a base such as an alkali metal hydrogen carbonate (e.g. sodium bicarbonate) or a tertiary amine (e.g. diisopropylethylamine) in a suitable solvent such as acetonitrile, an aromatic hydrocarbon (e.g. toluene), a substituted amide (e.g. dimethylformamide) or a ketone (e.g. methyl isobutyl ketone) and at an elevated temperature.

Compounds of formula (II) in which Y represents an acyloxy, alkoxycarbonyloxy or an imidazolide group may be prepared, for example, by reacting a compound of formula (VI):

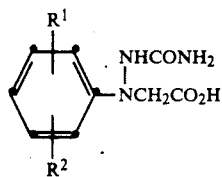 (VI)

or a salt thereof, with an appropriate acyl halide, alkyl chloroformate or imidazole derivative (e.g. N,N'-carbonyldiimidazole) respectively, using conventional techniques.

Compounds of formula (III) may be prepared, for example, by the reaction of a compound of formula (VII):

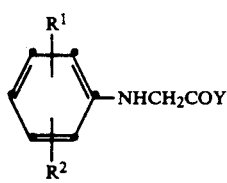 (VII)

wherein Y is as defined previously, or a protected derivative thereof, with an appropriate nitrosating agent (e.g. an aqueous solution of sodium nitrite in acetic acid) at 0° C., followed by reduction using a suitable reducing agent (e.g. zinc dust).

Compounds of formula (IV) are either known or may be prepared, for example, by the reaction of a compound of formula (VIII):

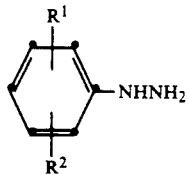 (VIII)

with urea. The reaction may conveniently be effected in a solvent such as water, and at the reflux temperature of the solvent.

Compounds of formula (VI) may be prepared by hydrolysis of a compound of formula (II) in which Y represents a leaving group using conventional techniques.

Compounds of formula (VII) are either known or may be prepared, for example, by the reaction of a compound of formula (IX):

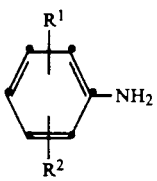 (IX)

with a compound of formula (V) in the presence of a base such as an alkali metal hydrogen carbonate (e.g. sodium bicarbonate) or sodium acetate trihydrate, optionally in a suitable solvent such as acetonitrile or an alcohol (e.g. methanol) and at an elevated temperature (conveniently the reflux temperature of the solvent).

The compounds of formulae (V), (VIII) and (IX) are either known or may be prepared from known compounds by conventional procedures.

According to another general process (B), a compound of formula (I) may be prepared by cyclising a compound of formula (X)

$$\text{(X)}$$

NHNHCONHCOCH₂L wherein L represents a leaving group, preferably a halogen atom (e.g. a chlorine or bromine atom).

The cyclisation may be effected in the same manner as the cyclisation of compounds of formula (II) above.

Compounds of formula (X) may be prepared by reacting a compound of formula (VIII) above with a compound of formula XI

LCH₂CONCO      (XI)

According to another general process (C), a triazine derivative of formula (I) may be converted into another triazine derivative of formula (I) using conventional techniques.

Thus, according to one embodiment of the interconversion process, a triazine derivative of formula (I) in which R¹ represents a hydroxy group may be prepared, for example, by hydrogenation of the corresponding triazine derivative of formula (I) in which $R^1$ represents a benzyloxy group.

Hydrogenation may conveniently be effected in the presence of a catalyst such as platinum or palladium on a charcoal support, in a solvent such as alcohol (e.g. ethanol or methanol), at normal or elevated temperature and pressure, for example from 20° to 100° C. and from 1 to 10 atmospheres.

A physiologically acceptable salt of a compound of formula (I) may be prepared by reacting a compound of formula (I) in the form of the free base with an appropriate acid or base using conventional methods.

Physiologically acceptable salts may also be prepared from other salts, including other physiologically acceptable salts, of a compound of formula (I) using conventional methods.

The various general methods described above may be used for the introduction of the desired groups at any stage in the stepwise formation of the required compound, and it will be appreciated that these general methods can be combined in different ways in such multi-step processes. The sequence of the reactions in multi-stage processes should of course be chosen so that the reaction conditions used do not affect groups in the molecule which are desired in the final product.

The invention is further illustrated by the following Preparations and Examples. All temperatures are in °C. Thin layer chromatography (t.l.c.) was carried out on silica, and flash column chromatography (FCC) was carried out on silica (Merck 9385). Petroleum ether refers to that fraction having b.p. 40°-60° C., unless otherwise stated. Organic extracts were dried over magnesium sulphate or sodium sulphate. Solvent system A denotes ether:petroleum ether and System B denotes ethyl acetate:petroleum ether.

INTERMEDIATE 1

N-(3-Bromophenyl)glycine methyl ester

A mixture of 3-bromoaniline (88.6 g), methyl chloroacetate (44 ml), sodium acetate trihydrate (114 g) and methanol (70 ml) was heated under reflux for 18 h. The mixture was poured into water (500 ml) and extracted with dichloromethane (3×250 ml). The combined, dried organic extracts were evaporated and the residue was treated with 10% concentrated sulphuric acid in methanol (250 ml). After 3 h the solution was poured carefully into 8% sodium bicarbonate (1200 ml). The resulting solid was filtered off, dissolved in dichloromethane (1000 ml), and this solution was dried and evaporated to give a solid (94 g). A portion of this solid (1 g) was purified by FCC eluting with System A (1:1) to give a semi-solid which was recrystallised from System A to give the title compound, m.p. 66°-68°.

INTERMEDIATE 2

N-(3-Fluorophenyl)glycine methyl ester

3-Fluoroaniline (55.5 g), methyl chloroacetate (44 ml), and sodium acetate trihydrate (114 g) were treated according to the method of Intermediate 1 to give a solid (50 g), a small sample of which (ca. 1 g) was purified by FCC eluting with System B (1:3) to give a solid which was recrystallised from petroleum ether (60°-80°) to give the title compound, m.p. 68°-69°.

INTERMEDIATE 3

N-(3-Methylphenyl)glycine methyl ester

A mixture of m-toluidine (55.0 g), methyl chloroacetate (85.0 g) and sodium bicarbonate (86.2 g) in acetonitrile (400 ml) was heated at reflux for 2 days under nitrogen. Ethyl acetate (250 ml) was added and the mixture was washed with water (2×250 ml), dried and evaporated to give an oil (120 g), a sample of which (1.4 g) was purified by FCC eluting with System A (3:7) to give the title compound (0.8 g) as a solid, m.p. 40°.

INTERMEDIATE 4

N-(3,4-Dimethylphenyl)glycine methyl ester 3,4-Dimethylaniline (70.0 g) and methyl bromoacetate (44.2 g) were stirred at 100° under nitrogen for 2 h. The cooled reaction mixture was poured into ether (700 ml) and filtered. The collected solid was washed with ether (2×100 ml) and the combined filtrates were concentrated to give a solid (45.6 g) which was purified by FCC on triethylamine deactivated silica eluting with dichloromethane: petroleum ether (1:3) to give a solid (21.8 g), a portion of which (2.5 g) was purified further by FCC as above to give the title compound (2.06 g), m.p. 53°-55°.

INTERMEDIATE 5

N-(3,4-Difluorophenyl)glycine methyl ester

A suspension of 3,4-difluoroaniline (15.0 g) and sodium bicarbonate (19.5 g) in methyl chloroacetate (15.2 ml) was stirred at 80°-90° under nitrogen for 16 h. The cooled reaction mixture was poured into ether (100 ml) and filtered. The filtrate was washed with 2N aqueous hydrochloric acid (100 ml), dried and concentrated to give a solid (16.5 g) which was recrystallised from dichloromethane (20 ml) and n-hexane (40 ml) to give the title compound (9.21 g), m.p. 71°-73°.

INTERMEDIATE 6

N-(3,5-Difluorophenyl)glycine methyl ester

A suspension of 3,5-difluoroaniline (15.0 g) and sodium bicarbonate (19.5 g) in methyl chloroacetate (15.2 ml) was stirred at 80°-90° under nitrogen for 60 h. More sodium bicarbonate (4.88 g) and methyl chloroacetate (5.1 ml) were added, and the suspension was stirred at 80°-90° for a further 24 h. Work up according to the method of Intermediate 5 gave a solid (16 g) which was recrystallised from chloroform (10 ml) and n-hexane (120 ml) to give the title compound (8.34 g), m.p. 75°-77°.

The mother liquors from the recrystallisation were concentrated and triturated with n-hexane (100 ml) to give a further amount of the title compound (1.83 g).

INTERMEDIATE 7

N-(3-Methoxyphenyl)glycine methyl ester

A mixture of 3-methoxyaniline (61.6 g), methyl chloroacetate (44 ml), sodium acetate trihydrate (114 g) and methanol (70 ml) was heated under reflux for 18 h. The mixture was poured into water (500 ml) and extracted with dichloromethane (3×250 ml). The combined, dried organic extracts were evaporated and the residue was treated with a 10% concentrated sulphuric acid in methanol (250 ml). After 3 h the solution was poured carefully into 8% sodium bicarbonate (1200 ml) and partitioned with ether (4×500 ml). The combined organic extracts were washed successively with 0.5M citric solution (5×200 ml) and brine (500 ml), dried and evaporated to give an oil. Purification by FCC eluting initially with ether:petroleum ether 60°-80° (2:3) and then with ether:petroleum ether 60°-80° (1:1) give the title compound (52 g) as an oil, t.l.c (System A, 1:1) Rf 0.31.

INTERMEDIATE 8

N-[3-phenylmethoxy)phenyl]glycine methyl ester

A suspension of 3-benzyloxyaniline (69.0 g) and sodium bicarbonate (58.1 g) in methyl chloroacetate (45.4 ml) was stirred at 80°-90° under nitrogen for 16 h. The resultant solid was poured into ether (400 ml) and the suspension was filtered. The collected solid was partitioned between water (400 ml) and dichloromethane (200 ml). The organic layer was separated and the aqueous layer was extracted with dichloromethane (2×200 ml). The combined organic extracts were dried and concentrated to give the title compound (66.9 g) as a solid, m.p. 92°-94°

INTERMEDIATE 9

N-[4-(Phenylmethoxy)phenyl]glycine methyl ester

4-Benzyloxyaniline hydrochloride (70 g), methyl chloroacetate (49 ml) and sodium bicarbonate (75 g) in dry acetonitrile (200 ml) were heated at reflux for 6.5 h. Work up according to the method of Intermediate 8 gave a solid which was recrystallised from chloroform-hexane to give the title compound (55 g), m.p. 106°-107°.

INTERMEDIATE 10

Methyl [1-(3-bromophenyl)hydrazino]acetate

A solution of sodium nitrite (30 g) in water (200 ml) was added dropwise to a solution of N-(3-bromophenyl)glycine methyl ester (94 g) in aqueous acetic acid (850 ml) at 0°. After 1 h, methanol (200 ml) was added and the mixture was cooled to −10°. Zinc dust (351 g) was added portionwise over 2 h during which time the temperature was maintained at −10° to 0°. The mixture was then allowed to warm to room temperature, poured into ethyl acetate (1000 ml) and filtered. The filtrate was poured into water (1000 ml) and the layers were separated. The organic extract was washed with 2N sodium carbonate solution (500 ml) and solid sodium carbonate was added until the solution was basic. The aqueous extract was re-extracted using ethyl acetate (1000 ml) and the combined organic extracts were dried and evaporated. The residue was purified by FCC eluting with System A (1:1) to give the title compound (25.1 g) as an oil, t.l.c. (System A, 1:1) Rf 0.26.

INTERMEDIATE 11

Methyl [1-(3-fluorophenyl)hydrazino]acetate

N-(3-(Fluorophenyl)glycine methyl ester (10.0 g) was treated according to the method of Intermediate 10, using zinc powder (14.3 g). The residue was purified by FCC eluting with ether:petroleum ether (60°-80°) (1:1) to give the title compound (4.56 g) as an oil, t.l.c. (ether:petroleum ether (60°-80°), 1:1) Rf 0.16.

INTERMEDIATE 12

Methyl [1-(3-methoxyphenyl)hydrazino]acetate

To a cold (0°) solution of N-(3-methoxyphenyl)glycine methyl ester (50 g) in aqueous acetic acid (800 ml) was added dropwise an aqueous solution (200 ml) of sodium nitrite (21.2 g) and the mixture was stirred for 30 min. Methanol (200 ml) was added and the mixture was cooled to −10°. Zinc dust (83.2 g) was added portionwise over 2 h during which time the internal temperature was maintained at −10° to 0° and the mixture was stirred for a further 1 h at 0°. Dichloromethane (800 ml) and water (800 ml) were added and the resulting suspension was filtered. The filtrate was diluted with more water (500 ml) and dichloromethane (500 ml). The phases were separated and the aqueous layer was partitioned with more dichloromethane (2×500 ml). The combined organic extracts were washed with water (3×500 ml) and evaporated in vacuo. The residual oil was treated with 8% sodium bicarbonate (1000 ml) and partitioned with ether (3×700 ml). The combined organic layers were washed with brine (500 ml), dried and evaporated. Purification by FCC eluting with System A (1:1) and then System A (7:3) gave the title compound (8.2 g) as an oil, t.l.c (System A, 1:1) Rf 0.12.

The residue was purified by FCC eluting with ether:petroleum ether (60°-80°) (1:1) to give the title compound (4.56 g) as an oil, t.l.c (ether:petroleum ether (60°-80°); 1:1 Rf 0.16.

Intermediates 13 to 21 were prepared in a similar manner to Intermediate 10, using only 3 to 5 equivalents of zinc dust, and in some cases the organic solution was basified with anhydrous sodium bicarbonate or with sodium bicarbonate solution instead of sodium carbonate. In addition, Intermediates 16 and 19 were prepared without the addition of methanol to the reaction mixture prior to adding the zinc dust.

INTERMEDIATE 13

Methyl [1-(3-methylphenyl)hydrazino]acetate

The title compound (18.0 g) was obtained as an oil, t.l.c. (System B, 1:9) Rf 0.15, from N-(3-methylphenyl)glycine methyl ester (116 g). The product was purified by FCC eluting with System B (1:9).

INTERMEDIATE 14

Methyl [1-(4-methylphenyl)hydrazino]acetate

The title compound (12.0 g) was obtained as an oil, t.l.c (ether) Rf 0.5, from N-(4-methylphenyl)glycine methyl ester (19.0 g). The product was isolated by extraction with dichloromethane (instead of ethyl acetate) and was purified by FCC eluting with System A (2:3).

INTERMEDIATE 15

Methyl [1-(4-fluorophenyl)hydrazino]acetate

The title compound (2.12 g) was obtained as an oil, t.l.c. (System B, 1:3) Rf 0.37, from N-(4-fluorophenyl)glycine methyl ester (15.0 g). The product was purified by FCC eluting with System B (1:3).

INTERMEDIATE 16

Methyl [1-(2-fluorophenyl)hydrazino]acetate

The title compound (5.7 g) was obtained as an oil, t.l.c. (System B, 2:5), from N-(2-fluorophenyl)glycine methyl ester (25.1 g). The product was purified by FCC eluting with System B (2:5).

The products of Intermediates 17 to 19 were purified by FCC eluting with chloroform.

INTERMEDIATE 17

Methyl [1-(3,4-dimethylphenyl)hydrazino]acetate

The title compound (6.25 g) was obtained as an oil, t.l.c. (chloroform) Rf 0.17, from N-(3,4-dimethylphenyl)glycine methyl ester (19.23 g).

INTERMEDIATE 18

Methyl [1-(3,4-difluorophenyl)hydrazino]acetate

The title compound (4.60 g) was obtained as an oil, t.l.c. (chloroform) Rf 0.2, from N-(3,4-difluorophenyl)glycine methyl ester (9.56 g).

INTERMEDIATE 19

Methyl [1-(3,5-difluorophenyl)hydrazino]acetate

The title compound (2.98 g) was obtained as an oil, t.l.c. (chloroform) Rf 0.21, from N-(3,5-difluorophenyl)glycine methyl ester (8.00 g).

INTERMEDIATE 20

Methyl[1-[3-(phenylmethoxy)phenyl]hydrazino]acetate

The title compound (4.56 g) was obtained as an oil t.l.c (System B, 1:5) Rf 0.36, from N-[3-(phenylmethoxy)phenyl]glycine methyl ester (22 g). The product was purified by FCC eluting with System B (1:5).

INTERMEDIATE 21

Methyl [1-[4-phenylmethoxy)phenyl]hydrazino]acetate

The title compound (6.02 g) was obtained as a solid, m.p. 72°-73°, from N-[4-(phenylmethoxy)phenyl]glycine methyl ester (50 g). The product was purified by FCC on triethylamine deactivated silica eluting with chloroform:petroleum ether (1:1).

EXAMPLE 1

Dihydro-1-(3-methylphenyl)-1,2,4-triazine-3,5-(2$\underline{H}$,4$\underline{H}$)-dione To a solution of methyl [1-(3-methylphenyl)hydrazino]acetate (2 g) and sodium cyanate (2 g) in dry toluene (125 ml) was added dropwise at 23° a solution of trifluoroacetic acid (2.37 ml) in dry toluene (25 ml). The mixture was stirred at 23° under nitrogen for 2.5 h, and then partitioned between 8% sodium bicarbonate solution (300 ml) and dichloromethane (300+200 ml). The combined organic extracts were washed with saturated brine (250 ml), dried and evaporated to give the intermediate urea as an oil.

This oil was dissolved in methanol (25 ml), and added dropwise to a solution of sodium methoxide (1.63M solution in methanol; 18.95 ml) at 23° under nitrogen. The mixture was stirred for 1 h, and was then poured into 15% phosphate buffer solution (150 ml) and extracted with ethyl acetate (2×100 ml). The combined, dried organic extracts were evaporated, and the residue was purified by FCC eluting with System B (2:1) to give a solid. Trituration and filtration of this solid afforded the title compound (137 mg).

T.l.c. (System B, 2:1) Rf 0.36.

$^1$H-N.m.r. indicated 0.18 mol ethyl acetate present.

Analysis found: C,58.6; H,5.5; N,19.0; $C_{10}H_{11}N_3O_2+0.18C_4H_8O_2$ requires C,58.3; H,5.6; N,19.0%.

Examples 2 to 12 were prepared in a similar manner to Example 1, i.e. by reaction of the appropriate hydrazino acetate with 3 mole equivalents of both sodium cyanate and trifluoroacetic acid in toluene at room temperature. The resulting mixture was then partitioned between sodium bicarbonate (or in the case of Example 3, phosphate buffer solution) and either dichloromethane or ethyl acetate. The organic extracts were dried and evaporated to give the intermediate urea which was dissolved in methanol and stirred with a solution of sodium methoxide in methanol at room temperature. (In Examples 4 and 5 the intermediate urea was first chromatographed on silica eluting with 2% methanol in ethyl acetate). The mixture was then poured into phosphate buffer solution, and extracted with either ethyl acetate or dichloromethane. The combined, dried organic extracts were evaporated and the product was purified by one of a variety of methods. Thus the products of Examples 2, 6, 7, 8, 9 and 11 were triturated with ether, the products of Examples 2 and 9 additionally being recrystallised from System B and from tetrahydrofuran/hexane respectively. The products of Examples 4 and 5 were triturated with ethyl acetate/ether. The product of Example 10 was dissolved in hot ethyl acetate, treated with charcoal, the solution filtered and the filtrate evaporated to ca. 10 ml; petroleum ether (60°-80°) was added until the solution was turbid and on cooling the product precipitated.

EXAMPLE 2

Dihydro-1-(3-bromophenyl)-1,2,4-triazine-3,5-(2$\underline{H}$,4$\underline{H}$)-dione From methyl [1-(3-bromophenyl)hydrazino]acetate (5.18 g) was obtained the title compound (1.4 g), m.p. 238°-240°.

Analysis found: C,40.2; H,3.0; N,15.3; $C_9H_8BrN_3O_2$ requires C,40.0; H,3.0; N,15.6%.

EXAMPLE 3

Dihydro-1-(3-fluorophenyl)-1,2,4-triazine-3,5-(2$\underline{H}$,4$\underline{H}$)-dione From methyl [1-(3-fluorophenyl)hydrazino]acetate (1.5 g) was obtained the title compound (0.53 g), m.p. 186°.

Analysis found: C,51.7; H,3.9; N,20.1; $C_{18}H_{30}N_2O_3$ requires C,51.7; H,3.8; N,19.7%.

EXAMPLE 4

Dihydro-1-(4-methylphenyl)-1,2,4-triazine-3,5-(2$\underline{H}$,4$\underline{H}$)-dione From methyl [1-(4-methylphenyl)hydrazino]acetate (500 mg) was obtained the title compound (218 mg), (which had been dried in vacuo at 44° for 4 h), m.p. 270° (decomp.).

T.l.c. (ethyl acetate) Rf 0.57.

EXAMPLE 5

Dihydro-1-(4-fluorophenyl)-1,2,4-triazine-3,5-(2$\underline{H}$,4$\underline{H}$)-dione From methyl [1-(4-fluorophenyl)hydrazino]acetate (2.67 g) was obtained the title compound (1.26 g), m.p. 232°-233°.

T.l.c. (System B, 1:2) Rf 0.1.

EXAMPLE 6

Dihydro-1-(2-fluorophenyl)-1,2,4-triazine-3,5-(2H,4H)-dione

From methyl [1-(2-fluorophenyl)hydrazino]acetate (2.80 g) was obtained the title compound (794 mg), m.p. 203°–205°.

T.l.c. (System B, 1:2) Rf 0.30.

EXAMPLE 7

Dihydro-1-(3,4-dimethylphenyl)-1,2,4-triazine-3,5-(2H,4H)-dione

From methyl [1-(3,4-dimethylphenyl)hydrazino]acetate (3.0 g) was obtained the title compound (0.772 g), m.p. 205°–206°.

T.l.c. (ethyl acetate) Rf 0.70.

EXAMPLE 8

Dihydro-1-(3,4-difluorophenyl)-1,2,4-triazine-3,5-(2H,4H)-dione

From methyl [1-(3,4-difluorophenyl)hydrazino]acetate (2.0 g) was obtained the title compound (0.283 g), m.p. 208°–210°.

Analysis found: C,47.4; H,3.1; N,18.4; $C_9H_7F_2N_3O_2$ requires C,47.6; H,3.1; N,18.5%.

EXAMPLE 9

Dihydro-1-(3,5-difluorophenyl)-1,2,4-triazine-3,5-(2H,4H)-dione

From methyl [1-(3,5-difluorophenyl)hydrazino]acetate (1.33 g) was obtained the title compound (0.131 g) (which had been dried at 60° and 0.1 torr for 16 h), m.p. 256°–258° (decomp.).

T.l.c. (ethyl acetate:chloroform, 1:1) Rf 0.45.

EXAMPLE 10

Dihydro-1-(3-methoxyphenyl)-1,2,4-triazine-3,5-(2H 4H)-dione

From methyl [1-(3-methoxyphenyl)hydrazino]acetate (1.95 g) was obtained the title compound (0.23 g), m.p. 210°–212°.

Analysis found: C,53.9; H,5.0; N,18.9; $C_{10}H_{11}N_3O_3$ requires C,54.3; H,5.0; N,19.0%.

EXAMPLE 11

Dihydro-1-[3-[(phenylmethoxy)phenyl]-1,2,4-triazine-3,5-(2H, 4H)-dione

From methyl [1-[3-(phenylmethoxy)phenyl]hydrazino]acetate (5.0 g) was obtained the title compound (1.97 g), a portion of which (0.97 g) was dried at 60° and 0.1 torr for 16 h to give the title compound (0.92 g), m.p. 171°–173°.

Analysis found: C,64.7; H,5.1; N,14.2; $C_{16}H_{15}N_3O_3$ requires C,64.6; H,5.1; N,14.1%

EXAMPLE 12

Dihydro-1-[4-(phenylmethoxy)phenyl]-1,2,4-triazine-3,5-(2H, 4H)-dione

From methyl [1-[4-(phenylmethoxy)phenyl]hydrazino]acetate (1.27 g) was obtained the title compound (0.70 g), m.p. 214°–220°.

T.l.c (ethyl acetate) Rf 0.33.

EXAMPLE 13

Dihydro-1-(3-methylphenyl)-1,2,4-triazine-3,5-(2H 4H)-dione (i) Methyl [2-(aminocarbonyl)-1-(3-methylphenyl)hydrazino]acetate A mixture of 2-(3-methylphenyl)hydrazinecarboxamide (5 g), DEA (10.5 ml) and methyl bromoacetate (4.5 ml) in toluene (100 ml) was heated under reflux for 20 h, and was then partitioned between ethyl acetate (200 ml) and water (200 ml). The organic layer was washed with water (2×100 ml) and saturated brine (100 ml) before being dried and evaporated in vacuo to leave an oil (6.1 g). This was purified by FCC eluting with ethyl acetate to give the title compound (4.4 g) as a solid, m.p. 68°–70° after recrystallisation from ethyl acetate and trituration with ether.

(ii) Dihydro-1-(3-methylphenyl)-1,2,4-triazine-3,5-(2H,4H)-dione

A solution of sodium methoxide (2.17M in methanol; 3 ml) was added to a stirred solution of methyl [2-(aminocarbonyl)-1-(3-methylphenyl)hydrazino]acetate (0.5 g) in methanol (1 ml), and the mixture was stirred at 20° for 1.0 h. Water (20 ml) was added, followed by pH 6.5 phosphate buffer solution (30 ml), and the mixture was extracted with ethyl acetate (3×80 ml). The combined extracts were washed with water (2×80 ml) and saturated brine (80 ml), dried, and evaporated in vacuo to give a solid which was triturated with ether (30 ml) to give the title compound (261 mg), m.p. 245°–247°.

T.l.c. (ethyl acetate) Rf 0.59.

EXAMPLE 14

Dihydro-1-(3-chlorophenyl)-1,2,4-triazine-3,5(2H,4H)-dione (a) N-3-(Chlorophenyl) glycine methyl ester (Intermediate 22)

Sodium bicarbonate (66 g, 0.79 mol), 3-chloroaniline (50 g, 0.39 mol) and methyl chloroacetate (51.5 ml, 0.59 mol) were mixed under nitrogen and the reaction mixture was heated to 80°–100° C. with stirring for 6 h. Heating at 90° C. was continued overnight. After this time, the cooled mixture was poured into ether (400 ml). The suspension was chilled to 0° C., then filtered, The solid filter cake was retained and the filtrate was washed with dilute hydrochloric acid (200 ml; 2M) to remove unreacted starting material. The organic phase was dried and concentrated in vacuo to give an oily solid. The filter cake previously obtained was dissolved in ethyl acetate (400 ml) and washed with water (2×200 ml) followed by dilute hydrochloric acid (200 ml, 2M). The organic phase was dried and concentrated in vacuo to give the title compound (16.4 g, 21%) as a white solid, m.p. 75°–76°. The oily solid obtained from the filtrate was triturated with ether:hexane (1:1) (300 ml) and filtered to give a further batch of the title compound (20 g, 26%) as a white solid.

(b) Methyl[1-(3-chlorophenyl)hydrazino]acetate (Intermediate 23)

Intermediate 22 (10 g, 50.1 mmol) was dissolved in acetic acid (50 ml) with gentle warming. Water (5 ml) was added and the mixture was cooled to between 0° C. and 5° C. Sodium nitrite (3.63 g, 52.6 mmol) in water (10 ml) was added slowly to the glycine solution maintaining the low temperature, and the mixture was stirred for 1 h. The reaction was cooled to −10° C. and zinc powder (13 g, 199 mmol) was added at such a rate as to maintain the temperature below 0° C. The reaction was stirred at 0° C. for a few minutes, and then more acetic acid (40 ml) and methanol (10 ml) was added. The reaction was stirred at 0° C. for 5 h then warmed to room temperature and poured into water (400 ml). The aqueous phase was extracted with ethyl acetate (3×300 ml) and the combined organics were washed with sodium bicarbonate solution until effervescence ceased. The organic solution was dried ($Na_2SO_4$) and concentrated in vacuo to give the crude product which was purified by chromatography on silica (500 g) eluted with dichloromethane followed by dichloromethane-ethyl acetate (4:1) to give the title compound as a dark yellow oil (3.25 g, 30%). T.l.c. $SiO_2$, ethyl acetate, Rf. 0.70.

(c) Dihydro 1-(3-chlorophenyl)-1,2,4-triazine-3,5(2H,4H)-dione

The hydrazine (Intermediate 23; 700 mg, 3.3 mmol) was dissolved in dry toluene (15 ml) under nitrogen, and sodium cyanate (0.74 g, 11.4 mmol) was added. Trifluoroacetic acid (0.8 ml, 10.4 mmol) was added slowly and the mixture was stirred at room temperature for 6 h. After this time, the crude material was poured onto saturated sodium bicarbonate solution (100 ml) and extracted with ethyl acetate (3×75 ml). The dried ($Na_2SO_4$) organic phases were concentrated in vacuo to give crude product as a colourless foam. The intermediate urea was dissolved in methanol (15 ml) under nitrogen and sodium methoxide (4.5 ml; 2.17M: 9.8 mmol) was added slowly. The reaction was stirred at room temperature for 3.5 h.

The reaction mixture was poured into pH 6.5 phosphate buffer (50 ml) and extracted with ethyl acetate (3×50 ml). The combined organic extracts were dried ($Na_2SO_4$) and concentrated in vacuo to give an off white crystalline solid. The crude material was triturated with ether (2×20 ml) and filtered to give the title compound as a white solid (340 mg, 46%), m.p. 224°–226° (sublimes at ca. 190°).

T.l.c.: $SiO_2$, EtOAc, Rf 0.64.

EXAMPLE 15

Dihydro-1-(4-chlorophenyl)-1,2,4-triazine-3,5-(2H,4H)-dione (a) N-(4-Chlorophenyl)glycine methyl ester (Intermediate 24)

A mixture of sodium bicarbonate (66.0 g, 0.79 mmol), 4-chloroaniline (50 g, 0.39 mol) and methyl chloroacetate (51.5 ml, 0.59 mol) was heated at ca 80° C. overnight to afford a solid product. This material was crushed to a fine powder and washed with water (200 ml) and ethyl acetate (2×150 ml). A fraction (50 g) of the resultant solid (80 g) was recrystallised from absolute ethanol to afford a white crystalline product (31 g, 40%), m.p. 111°–114°. T.l.c $SiO_2$ triethylamine deactivated, hexane/ethyl acetate (1:1), Rf 0.67.

(b) Methyl [1-(4-chlorophenyl)hydrazino]acetate(Intermediate 25)

The glycine (Intermediate 24, 15.0 g, 0.075 mol) was suspended in glacial acetic acid (50 ml) and water (10 ml), the mixture was cooled in an ice bath and a solution of sodium nitrite (5.4 g, 0.078 mmol) in water (20 ml) as added dropwise at such a rate as to maintain a reaction temperature below 15° C. On completion of the addition, the mixture was stirred at room temperature for ca. 90 mins prior to cautious addition of zinc dust (20.5 g, 0.30 mol), in small portions, at such a rate as to maintain a temperature of below 25° C. The reaction was stirred at room temperature for a further ca. 3 h, then poured into water (400 ml) and extracted with ethyl acetate (3×100 ml). The combined extracts were neutralized with aqueous sodium hydrogen carbonate (ca. 120 g sodium hydrogen carbonate); washed with water (250 ml), dried and evaporated to afford a yellow moist solid. This material was triturated with ether (50 ml) to afford a white solid.

The triturant was evaporated to afford an orange oil (8.3 g) which was subjected to FCC on silica gel (450 g) using hexane/ethyl acetate (3.5:1) as the eluent. The title compound (Intermediate 25) was obtained as a light yellow oil (3.17 g, 19.7%).

T.l.c. $SiO_2$, hexane/ethyl acetate (1:1) Rf 0.62.

(c) Methyl[1-(4-chlorophenyl)-2-[(aminocarbonyl)hydrazino]acetate (Intermediate 26)

The hydrazine (Intermediate 25, 1.00 g, 4.7 mmol) was dissolved in dry toluene (50 ml) and sodium cyanate (0.97 g, 14.9 mmol) was added. Trifluoroacetic acid (1.04 ml, 13.6 mmol) was then added and the resultant mixture was stirred under nitrogen at ca. 50° for ca. 3 h. The resulting viscous insoluble gum was treated with 8% aqueous sodium hydrogen carbonate (50 ml) and extracted with ethyl acetate (3×75 ml). The combined extracts were washed with brine and dried. Removal of the solvent by evaporation gave a light yellow foam which was triturated with hexane/ethyl acetate (3:1) (15 ml) to afford the title compound (Intermediate 26) as a white powder (0.98 g, 82%), m.p. 124°–126°.

T.l.c $SiO_2$ ethyl acetate, Rf 0.20.

(d) Dihydro-1-[4-chlorophenyl]-1,2,4-triazine-3,5-(2H,4H)dione

Sodium methoxide (0.29 g, 5.4 mmol) was added under nitrogen to a stirred solution of the urea(Intermediate 26, 0.70 g, 2.72 mmol) in dimethoxyethane (20 ml) over 4A molecular sieves. After ca. 30 min the mixture was added to pH6.5 aqueous phosphate buffer (50 ml) and extracted with ethyl acetate (3×100 ml). The combined extracts were washed with brine (50 ml) dried and evaporated to afford a light yellow solid. Trituration with hexane/ethyl acetate (2:1) gave the title compound as a white powder (0.49 g, 80%). m.p. 265°–270° (dec). T.l.c. $SiO_2$, hexane/ethyl acetate (1:1), Rf 0.23.

EXAMPLE 16

Dihydro-1-(3-iodophenyl)-1,2,4-triazine-3,5-(2H,4H)-dione (a) N-(3-Iodophenyl) glycine methyl ester (Intermediate 27)

A mixture of 3-iodoaniline (40.0 g), methyl chloroacetate (37.12 g) and sodium bicarbonate (30.75 g) was heated in acetonitrile (400 ml) at reflux for 2 days under nitrogen. Ethyl acetate (250 ml) was then added and the mixture was washed with water (2×250 ml) dried and evaporated to give an oil (ca. 80 g), a sample of which (1.2 g) was purified by FCC eluting with ether-petroleum ether (7–3) to give the title compound (Intermediate 27; 0.8 g) as a solid, m.p. 83°.

(b) Methyl[1-(3-iodophenyl)hydrazino]acetate (Intermediate 28)

A solution of sodium nitrite (16.15 g) in water (50 ml) was added dropwise to a solution of N-(3-iodophenyl)-glycine methyl ester (Intermediate 27; 61.0 g) in aqueous acetic acid (850 ml) at 0°. After 1 h, methanol (110 ml) was added and the mixture was cooled to −10°. Zinc dust (50 g) was added portionwise over 2 h during which time the temperature was maintained at −10° to 0°. The mixture was then allowed to warm to room temperature, poured into ethyl acetate (200 ml) and filtered. The filtrate was poured in to water (400 ml) and the layers were separated. The organic extract was washed with 2N sodium carbonate solution (200 ml) and solid sodium carbonate was added until the solution was basic. The aqueous extracts was reextracted using ethyl acetate (200 ml) and the combined organic extracts were dried and evaporated to give an oil (20.1 g). The product was purified by FCC eluting with ethyl acetate:petroleum ether (1:4), and a portion was then rechromatographed under the same conditions to give methyl [1-(3-iodophenyl)hydrazino]acetate (0.7 g).

T.l.c, $SiO_2$; ethyl acetate:petroleum ether (1:4); Rf 0.13.

(c) Methyl [2-(aminocarbonyl)-1-[3-(iodophenyl)hydrazino]acetate (Intermediate 29)

A solution of trifluoroacetic acid (18.5 mg; 27.4 g; 242 mmol) in dry toluene (200 ml) was added dropwise to a mixture of the hydrazine (Intermediate 28; 23.98 g; 78 mmol) and sodium cyanate (15.67 g; 242 mmol) in dry toluene (800 ml) at 23° under nitrogen. After 1.75 h, the suspension was concentrated to ca 400 ml then poured into 8% sodium bicarbonate solution (1000 ml) and extracted with dichloromethane (3×600 ml). The combined extracts were washed with saturated brine (1000 ml), dried and evaporated. The residual solid was triturated with ethyl acetate-ether, filtered and dried in vacuo to give the urea (Intermediate 29, 20.7 g; 76%) as a white powder with m.p. 165°–167°.

T.l.c $SiO_2$-EtOAc, Rf 0.2.

(d) Dihydro-1-(3-iodophenyl)-1,2,4-triazine-3,5(2H,4H)-dione

A solution of sodium methoxide in methanol (2.17M-2.76 ml; 6 mmol) was added to a suspension of the urea (Intermediate 29, 700 mg; 2 mmol) in methanol (10 ml) at 23°. The mixture was stirred under nitrogen for 1.5 h then poured into 15% phosphate buffer solution (200 ml) and extracted with chloroform (3×100 ml) and ethyl acetate (100 ml). The combined, dried extracts were evaporated and the residue triturated with ethyl acetate to give the triazinedione (305 mg; 48%) as a cream solid with m.p. >250°.

T.l.c $SiO2$; EtOAc. Rf 0.63.

EXAMPLE 17

Dihydro-1-[3-(1-methylethyl)phenyl]-1,2,4-triazine-3,5-(2H, 4H)-dione (a) Methyl[(2-aminocarbonyl)-1-(3-(2'-methylethenyl)phenyl) hydrazino]acetate (Intermediate 30)

A suspension of silver oxide (1.5 g, 5 mmol), isopropenyl boronic acid (2.5 ml of a 5 ml solution containing 0.89 g, 4.9 mmol), palladium tetrakistriphenylphosphine (200 mg, 25%), and iodide (Intermediate 29; 0.57 g, 1.63 mmol) in dry, freshly distilled tetrahydrofuran (6.5 ml) was stirred for 30 min at room temperature under nitrogen. The reaction was then filtered, quenched (pH 6.5 phosphate buffer) extracted with ethyl acetate, washed with water and saturated sodium chloride, dried ($Na_2SO_4$) and concentrated. Flash chromatography ($SiO_2$, 5% methanol in dichloromethane) afforded the title compound (Intermediate 30; 0.466 g) as a colourless oil.

T.l.c. $SiO_2$ EtOAc; Rf 0.63.

(b) Dihydro-1-[3-(2'-methylethenyl)phenyl]-1,2,4-triazine-3,5-(2H,4H)-dione (Intermediate 31)

Sodium methoxide (0.185 mg, 3.42 mmol) was added to a suspension of urea (Intermediate 30) (0.45 g, 1.17 mmol) in dry dimethoxyethane (17 ml) with 4A molecular sieves. After stirring at room temperature for 15 min the reaction mixture was poured into pH 6.5 phosphate buffer, extracted with ethyl acetate, washed with water and saturated sodium chloride, dried ($Na_2SO_4$) and concentrated. The solid residue was taken up in ethyl acetate filtered, evaporated and triturated with ether to afford the title compound (Intermediate 31, 0.133 g, 31%) as an off white solid m.p. 178°–180°. The mother liquor afforded a further 70 mg (15%) of the title compound.

T.l.c. $SiO_2$; 5% MeOH in $CH_2Cl_2$; Rf 0.50.

(c) Dihydro-1-[3-(1-methylethyl)phenyl]-1,2,4-triazine-3,5-(2H,4H)-dione

A hydrogen saturated suspension of Intermediate 31 (70.0 mg, 0.28 mmol) and 5% palladium on carbon (30 mg) in ethanol (14 ml) was stirred under hydrogen until hydrogen absorption was complete (1 h). The suspension was degassed, filtered through celite and concentrated. The residue was subjected to FCC ($SiO_2$, 5% methanol in dichloromethane) to afford the title compound as a white solid m.p. 130°–132°, (45 mg, 65%).

T.l.c. $SiO_2$; 5% MeOH in $CH_2Cl_2$, Rf 0.40.

EXAMPLE 18

Dihydro-1-(3-propylphenyl)-1,2,4-triazine-3,5(2H,4H)-dione (a) N-(3-Propylphenyl)glycine methyl ester (Intermediate 32)

3-n-Propyl-aniline (20 g, 148 mmol), sodium bicarbonate (24.9 g, 296 mmol) and methyl chloroacetate (24.0 g, 221 mmol) were mixed under nitrogen and stirred at 80°–90° C. for 24 h. The cooled reaction was poured into ether (100 ml) and filtered. The filtrate was washed with water (100 ml), dilute hydrochloric acid (100 ml) and water (100 ml), then dried and concentrated in vacuo. The oily product (21.2 g) was distilled on the Kugelrohr collecting the fraction boiling at 160°/0.35 mmHg to give the title compound (Intermediate 32) as a colourless liquid which solidified into a pale yellow, low melting solid (16.1 g, 53%).

T.l.c. $SiO_2$, Chloroform-ethanol 98:2, Rf 0.67.

(b) Methyl [1-(3-propylphenyl)hydrazino]acetate (Intermediate 33)

Glycine (Intermediate 32, 10 g, 48 mmol) was dissolved in acetic acid (50 ml) and water (5 ml). The solution was cooled to 0° C. and sodium nitrite (3.67 g, .53 mmol) in water (10 ml) was added such that the temperature did not rise above 5° C. The yellow solution turned red then brown, and was stirred at 0° C. for 1 h. The mixture was cooled to −5° C. and zinc powder (12.6 g, 193 mmol) was added very slowly such that the temperature did not rise above 0° C. The mixture was stirred at 0° C. for 5 h then poured into water (400 ml) and extracted with ethyl acetate (3×150 ml). The combined, dried ($Na_2SO_4$) organic extracts were concentrated in vacuo to give a dark yellow oil. The crude material was purified by chromatography on silica (500 g) eluted with chloroform-ethanol 98:2 to give the title compound (Intermediate 33, 1.4 g, 13%) as a yellow oil.

T.l.c. $SiO_2$; Chloroform-ethanol 98:2; Rf 0.17.

(c) Methyl [2-(aminocarbonyl)-1-(3-propylphenyl)hydrazino]acetate (Intermediate 34)

The hydrazine (Intermediate 33; 910 mg, 4.1 mmol) was dissolved in dry toluene (30 ml) under nitrogen at room temperature. Sodium cyanate (880 mg, 13.5 mmol) was added to the reaction mixture, followed by trifluoroacetic acid (0.95 ml, 12.3 mmol). The reaction was stirred at room temperature for 3 h, then poured into sodium bicarbonate solution (30 ml, 8%) and extracted with ethyl acetate (3×75 ml). The combined dried ($Na_2SO_4$), organic phases were concentrated in vacuo to give a yellow oil. The crude material was triturated with ether and hexane to give the title compound (Intermediate 34; 500 mg, 46%) as a white powdery solid m.p. 111°–116°.

T.l.c. $SiO_2$, ethyl acetate; Rf 0.26.

(d) Dihydro-1-(3-propylphenyl)-1,2,4-triazine-3,5(2H,4H)-dione

Urea (Intermediate 34; 316 mg, 1.2 mmol) was dissolved in methanol (20 ml) under nitrogen at room temperature and solid sodium methoxide (130 mg, 2.4 mmol) was added in one portion. The reaction was stirred for 4.5 h, then poured into pH 6.5 phosphate buffer solution (50 ml) and extracted with ethyl acetate (3×25 ml). The combined, dried ($Na_2SO_4$), extracts were concentrated in vacuo to give an orange solid.

The crude material was triturated with ether (4×20 ml) to give the title compound as a white powder (110 mg, 40%) m.p. 188°–190° C.

T.l.c. $SiO_2$; ethyl acetate, Rf 0.63.

EXAMPLE 19

Dihydro-1-(3,5-dimethylphenyl)-1,2,4-triazine-3,5(2H,4H)-dione (a) N-(3,5-Dimethylphenyl)glycine methyl ester (Intermediate 35)

A mixture of sodium hydrogen carbonate (66.0 g, 0.79 mol), 3,5-dimethylaniline (47.5 g, 0.39 mol) and methyl chloroacetate (51.5 ml, 0.59 mol) was rapidly stirred and heated at ca 80° C. overnight.

The mixture was cooled to room temperature and ethyl acetate (150 ml) and water (150 ml) was added to the resultant suspension. The material remaining undissolved was removed by filtration. The organic phase was separated, dried and evaporated to afford a brown solid. This material was triturated with ether (2×50 ml) to afford a white solid which was combined with the previously obtained solid to give a total of 67 g. This material was rapidly stirred in boiling chloroform (250 ml) and any undissolved material was removed by filtration. Evaporation of the filtrate afforded a light yellow solid (47.5 g) which was recrystallised from hexane/chloroform to yield the glycine (Intermediate 35) as light yellow crystals (32.5 g, 43%), m.p. 74°–76°. T.l.c. $SiO_2$; triethylamine deactivated; hexane/ethyl acetate (3:1); Rf 0.6.

(b) Methyl [1-(3,5-dimethylphenyl)hydrazino]acetate (Intermediate 36)

The glycine (Intermediate 35; 10.0 g, 0.052 mol) was dissolved in glacial acetic acid (75 ml), and water (5 ml) was added to the solution. After cooling to ca 5° C. a solution of sodium nitrite (3.80 g, 0.055 mol) in water (10 ml) was added dropwise, with stirring at such a rate as to maintain a reaction temperature below 5° C. The reaction was stirred at this temperature for a further 0.5 h before cautious addition of zinc powder (13.6 g, 0.21 mol) at such a rate as to keep the reaction temperature below 25° C. The mixture was then stirred overnight at room temperature before being poured into water (400 ml) and extracted with ethyl acetate (3×300 ml). The combined extracts were cautiously neutralised by addition of saturated aqueous sodium bicarbonate until effervescence ceased, the organic phase was separated, washed with water (150 ml) and dried. Removal of the solvent afforded a yellow solid/oil (9.75 g). This material was triturated with ether (2×25 ml) to afford starting material (4.1 g).

The combined triturants were evaporated and subjected to FCC on silica gel (300 g) using hexane/ethylacetate (6.5:1) as the eluent to afford a further quantity of the starting glycine and the title compound (Intermediate 36) as an orange solid (3.50 g).

Trituration of this material with hexane (2×15 ml) afforded methyl [1-(3,5-dimethylphenyl)hydrazino]acetate as a white solid (2.10 g, 19%), m.p. 56°–58°.

T.l.c. $SiO_2$; hexane/ethyl acetate (3:1); Rf 0.3.

(c) Methyl [2-(aminocarbonyl)-1-(3,5-dimethylphenyl)hydrazino]acetate (Intermediate 37)

Trifluoroacetic acid (1.06 ml, 13.9 mmol) was added under nitrogen to a stirred suspension of sodium cyanate (1.00 g, 15.2 mmol) in a solution of the hydrazine (Intermediate 36; 1.00 g, 4.8 mmol) in dry toluene (30 ml). The mixture was stirred for ca. 2 h, causing formation of a viscous insoluble gum. Saturated aqueous sodium hydrogen carbonate (25 ml) was added (causing effervescence and dissolution of the gum) and the mixture was extracted with ethyl acetate (3×75 ml). The combined extracts were washed with saturated brine (50 ml) dried and evaporated to afford a light yellow solid which was triturated with hexane/ethyl acetate (1:1) to give the title compound as a white powder (0.92 g, 76%), m.p. 139°–141°.

T.l.c. $SiO_2$; ethyl acetate; Rf 0.25.

(d) Dihydro-1-[3,5-dimethylphenyl]-1,2,4-triazine-3,5(2H,4H)dione

Sodium methoxide (0.32 g, 5.96 mmol) was added to a stirred solution of the urea (Intermediate 37; 0.75 g, 2.98 mmol) in dimethoxyethane (30 ml) over 4A sieves under a nitrogen atmosphere. After stirring at room temperature for ca. 30 min the resultant slurry was added to pH 6.5 aqueous phosphate buffer (50 ml) and extracted with ethyl acetate (3×75 ml). The combined extracts were washed with saturated brine (50 ml), dried and evaporated to afford an orange solid. Trituration of this material with hexane/ether (1:1) (2×15 ml) gave the title compound as a light pink solid (0.52 g, 64%), m.p. ca 255° (dec.).

T.l.c. SiO$_2$; ethyl acetate/hexane (1:1), Rf 0.33.

EXAMPLE 20

Dihydro-1-[3-ethylphenyl]-1,2,4-triazine-3,5(2H,4H)-dione

(a) N-(3-Ethylphenyl)glycine, methyl ester (Intermediate 38)

To m-ethylaniline (50 g; 0.413 mol) and sodium bicarbonate (69.33 g; 0.825 mol) was added methyl chloroacetate (39.79 ml; 0.454 mol) and acetonitrile (50 ml). The mixture was allowed to heat to 130° with stirring from 48 hours. The mixture was then taken up in ether. The ether extract was treated with 2N hydrochloric acid, after which the acid layer was extracted with ether. The combined organic extracts were washed with water, brine and then dried (Na$_2$SO$_4$). Filtration and evaporation of the solvent gave the title compound (36.95 g: 46%) as an oil.

T.l.c. SiO$_2$; ethyl ether: Petroleum ether (1:1); Rf 0.75.

(b) Methyl[1-(3-ethylphenyl)hydrazino]acetate (Intermediate 39)

To the glycine (Intermediate 38; 35 g; 0.181 mol) in acetic acid (50 ml) at −5° C. was added, dropwise, a solution of sodium nitrite (13.75 g; 0.199 mol) in H$_2$O (10 ml). The temperature of the reaction mixture was not allowed to rise above 0°. After stirring for a further 2 h, zinc dust (26.02 g, 0.398 mol) was added portionwise, once again so as not to allow the temperature of the reaction mixture to rise above 0°. After 5 h, a further quantity of zinc dust (13.01 g, 0.199 mol) was added and the mixture was stirred overnight. The excess zinc dust was removed by filtration through celite. The reaction mixture was then quenched with sodium bicarbonate solution. Extraction into ethyl acetate followed by washing with water, brine and finally drying (over Na$_2$SO$_4$) gave the crude title compound (ca. 35 g). This crude material was chromatographed using Ethyl acetate: Petroleum ether (1:3) to yield Intermediate 39 (5.21 g; 14%) as an oil.

T.l.c. SiO$_2$; Ethyl acetate - Petroleum Ether : 1:3, Rf 0.25.

(c) Methyl [2-(aminocarbonyl)-1-(3-ethylphenyl)hydrazino]acetate (Intermediate 40)

To the hydrazine (Intermediate 39; 3.75 g; 0.018 mol) and sodium cyanate (3.54 g; 0.054 mol) in toluene (30 ml) was added, dropwise, trifluoroacetic acid (5.82 g; 3.93 ml; 0.051 mol). This mixture was stirred for 3 h. and was then quenched with sodium bicarbonate and extracted into ethyl acetate. The organic extract was washed with sodium bicarbonate, water and brine and then dried (Na$_2$SO$_4$). Filtration and evaporation gave a cream solid which, on trituration with ether, afforded the title compound as a white solid (2.21 g; 49%), m.p. 128°–130° C.

T.l.c. SiO$_2$; Ether; Rf 0.3.

(d) Dihydro-1-[3-(ethylphenyl)]-1,2,4-triazine-3,5-(2H,4H)-dione

To the urea (Intermediate 40: 1.9 g; 8 mmol) in methanol (30 ml) was added sodium methoxide (612 mg; 11 mmol) in methanol (10 ml). The mixture was left at room temperature for 14 hours. The solvent was then removed and the mixture was quenched with 2.0N hydrochloric acid. The product was extracted with chloroform, washed with water and brine and then dried (Na$_2$SO$_4$). Filtration and evaporation gave an off-white solid, which was crystallised from methanol and then recrystallised from dioxan to give the title compound, m.p. 238° (dec.).

T.l.c. SiO$_2$; Ethyl acetate; Rf 0.75.

EXAMPLE 21

Dihydro-1-[3-(trifluoromethyl)phenyl]-1,2,4-triazine-3,5(2H,4H)-dione

(a) N-[3-(Trifluoromethyl)phenyl]glycine methyl ester (Intermediate 41)

A mixture of 3-trifluoromethylaniline (80.5 g), methyl chloroacetate (44 ml) and sodium acetate trihydrate (114 g) was heated in methanol (70 ml) under reflux for 18 h. The mixture was poured into water (500 ml) and extracted with dichloromethane (3×250 ml). The combined dried organic extracts were evaporated and the residue was treated with 10% concentrated sulphuric acid in methanol (250 ml). After 3 h the solution was poured carefully into 8% sodium bicarbonate (1200 ml). The resulting solid was filtered off, dissolved in dichloromethane (100 ml), and this solution was dried and evaporated to give a solid (84 g). A portion of this solid (1 g) was purified by FCC eluting with ether:petroleum (1:1) to give a solid which was recrystallised from ether-petroleum ether to give the title compound (Intermediate 41), m.p. 60°–63°

(b) Methyl-[3-(trifluoromethyl)phenyl]hydrazino]acetate (Intermediate 42)

To a cold (0°) solution of N-[3-trifluoromethyl)-phenyl]glycine methyl ester (Intermediate 41; 84 g) in aqueous acetic acid (850 ml) was added dropwise an aqueous solution (200 ml) of sodium nitrite (30 g) and the mixture was stirred for 30 min. Methanol (200 ml) was added and the mixture was cooled to −10°. Zinc dust (117 g) was added portionwise over 2 h during which time the internal temperature was maintained at −10° to 0° and mixture was stirred for a further 1 h at 0°.

Ethyl acetate (250 ml) was added and the resulting suspension was filtered. The filtrate was diluted with water (2000 ml) and extracted with ethyl acetate (3×2000 ml). The combined organic extracts were washed with 2N sodium carbonate (2000 ml), dried and evaporated. Purification by FCC, eluting with ethyl acetate - Petroleum ether (1:3), then gave the title compound (Intermediate 42; 22.2 g) as an oil.

T.l.c. SiO$_2$-EtOAc - petroleum ether (1:1)- Rf 0.28.

(c) Dihydro-1-[3-(trifluoromethyl)phenyl]-1,2,4-triazine-3,5-(2H,4H)-dione

Trifluoroacetic acid (0.93 ml, 12.1 mmol)) was added at 25° to a stirred suspension of the hydrazine (Intermediate 42; 1 g, 4.03 mmol) and sodium cyanate (0.91 g, 14.07 mmol) in toluene (15 ml). The bright orange solution was stirred at 25° for 2 h during which time an oil was precipitated. The mixture was treated with 8% sodium bicarbonate (50 ml) and extracted with ethyl acetate (3×50 ml). The combined extracts were washed with water (2×50 ml) and saturated brine (50 ml) before drying ($Na_2SO_4$) and evaporating in vacuo to a yellow solid. The solid was dissolved in methanol (10 ml) and treated at 25° with sodium methoxide (0.65 g, 12.1 mmol) in methanol (10 ml). The bright yellow solution was stirred at 25° for 0.5 h before pouring into pH 6.5 buffer (100 ml) and extracting with ethyl acetate (3×50 ml). The combined extracts were washed with water (2×50 ml) and saturated brine (50 ml) before drying ($Na_2SO_4$) and evaporating in vacuo to leave the crude product as a yellow solid. Trituration with diethyl ether (1×20 ml, 1×10 ml) gave the title compound as a white solid (102 mg) with m.p. 298°–305° (dec).

T.l.c, $SiO_2$ Ethyl Acetate, Rf 0.67.

EXAMPLE 22

Dihydro-1-[3-(1-methylethoxy)phenyl]-1,2,4-triazine-3,5(2H,4H)-dione (a) 3-(1-Methylethoxy)nitrobenzene (Intermediate 43)

A mixture of 3-nitrophenol (20 g; 144 mmol), 2-iodopropane (21.45 m 36.6 g; 216 mmol) and potassium carbonate (23.8 g; 172 mmol) in dimethylformamide (100 ml) was stirred at 50° for 2 h and then the temperature was increased to 70° for a further 2 h. More 2-iodopropane (7.15 ml; 72 mmol) was added and stirring at 70° continued for a further 1.5 h whereupon the mixture was poured into water (400 ml) and extracted with ethyl acetate (2×400 ml). The combined organic extracts were washed with sodium hydroxide (300 ml), then saturated brine (300 ml), dried and evaporated. The residue was chromatographed on silica (675 g) using petroleum ether (40°–60°)-ethyl acetate (10:1) as eluant to give the title compound (Intermediate 43; 22.37 g; 86%) as a yellow oil.

T.l.c. $SiO_2$ Petroleum ether (40°–60°):ether (9:1); Rf 0.4.

(b) 3-(1-Methylethoxy)benzeneamine (Intermediate 44)

A solution of the nitrobenzene (Intermediate 43; 20 g; 0.11 mol) in ethanol (1 l) was hydrogenated at 23° and atmospheric pressure in the presence of 10% palladium on charcoal (1.9 g) as catalyst. After 3 h, when hydrogen uptake had ceased (7392 ml; 0.33 mol), the mixture was filtered through hyflo and the filtrate evaporated to give the aniline (Intermediate 44; 14.6 g, 88%) as a red oil.

T.l.c. $SiO_2$; petroleum ether (40°–60°): ethyl acetate (7:1); Rf 0.34.

(c) N-[3-(1-Methylethoxy)phenyl]glycine methyl ester (Intermediate 45)

A mixture of 3-(1-methylethoxy)benzeneamine (Intermediate 44; 30 g; 0.198 mol), sodium bicarbonate (33.3 g, 0.396 mol) and methyl chloroacetate (26 ml, 0.297 mol) in acetonitrile (30 ml) was heated at 90° for 20 h.

Water (250 ml) was added and the mixture was extracted with ethyl acetate (3×250 ml). The organic extracts were washed with 2N hydrochloric acid (3×250 ml), water (250 ml) and saturated brine (250 ml) before drying ($Na_2SO_4$) and evaporating in vacuo to leave the title compound (Intermediate 45) as a pale brown oil (29.5 g; 66.6%).

T.l.c. $SiO_2$, Ethyl acetate-hexane (1:1), Rf 0.69%.

(d) Methyl [1-[3-(1-methylethoxy)phenyl]hydrazino]acetate (Intermediate 46)

A solution of sodium nitrite (2.4 g, 34.5 mmol) in water (15 ml) was added over 0.5 h at 0°–5° to a stirred solution of the glycine (Intermediate 45; 7 g, 31.5 mmol) in glacial acetic acid (70 ml) and methanol (10 ml). The now dark brown solution was stirred at $\leq 0°$ for 1.5 h before cooling to $-10°$ and treating with zinc dust (7.17 g, 0.11 mol) over 0.75 h at $\leq -5°$. The mixture was stirred at $\leq 10°$ for 1.5 h before filtering through hyflo into water (100 ml) and extracting with ethyl acetate (3×100 ml). The combined extracts were washed with water (2×100 ml) and treated with solid sodium carbonate and water (100 ml). The layers were separated and the organic portion washed with 2N sodium carbonate (100 ml), water (2×100 ml) and saturated brine (100 ml) before drying and evaporating in vacuo to leave a crude brown oil containing starting material and hydrazine (Intermediate 46; 6.7 g).

Column chromatography on triethylamine deactivated silica (250 g) eluting with chloroform-hexane (1:1) gave the title compound (Intermediate 46) as as brown oil (2.5 g; 33.3%).

T.l.c. Triethylamine deactivated $SiO_2$; chloroform-hexane (1:1); Rf 0.27.

(e) Dihydro-1-[3-(1-methylethoxy)phenyl]-1,2,4-triazine-3,5-(2H,4H)-dione

Trifluoracetic acid (0.97 ml, 12.6 mmol) was added to a stirred suspension of the hydrazine (Intermediate 46; 1 g, 4.2 mmol) and sodium cyanate (0.96 g, 14.7 mmol) in toluene (15 ml). The now bright yellow solution was stirred at 25° for 1.5 h during which time on oil was precipitated. 8% Aqueous sodium bicarbonate (50 ml) was added and the mixture was extracted with ethyl acetate (3×50 ml). The combined extracts were washed with water (2×50 ml) and saturated brine (50 ml) before drying ($Na_2SO_4$) and evaporating in vacuo to give the crude intermediate urea as a pale yellow oil.

The oil was dissolved in methanol (20 ml) and treated with sodium methoxide (0.68 g, 12.6 mmol) in methanol (10 ml). The bright yellow solution was then stirred at 25° for 1.0 h. The mixture was poured into pH 6.5 buffer (100 ml) and extracted with ethyl acetate (3×50 ml). The combined extracts were washed with water (3×50 ml) and saturated brine (50 ml) before drying ($Na_2SO_4$) and evaporating in vacuo to give the crude title compound as a pale yellow foam.

Trituration with isopropanol (20 ml) give the title compound as a white solid (110 mg; 10.5%) with m.p. 170°–172°.

T.l.c. $SiO_2$, Ethyl acetate, Rf 0.66.

The mother liquors from the trituration were evaporated to a yellow foam and re-trituration with isopropanol-hexane (1:1), (10 ml) gave a further sample of title compound as a pale cream solid (87 mg; 8.3%) with m.p. 168°–171°.

EXAMPLE 23

Dihydro-1-(3-butyloxyphenyl)-1,2,4-triazine-3,5(2H,4H)-dione (a) Methyl [1-(3-butyloxyphenyl)hydrazino]acetate (Intermediate 47)

Sodium nitrite (2.68 g, 38.9 mmol) in water (10 ml) was added dropwise to a solution of glycine N-[3-(n-butyloxyphenyl)]glycine methyl ester (8.8 g, 37.1 mmol) in acetic acid (50 ml) at −5° C. The temperature did not exceed −2° C. After stirring for 1 h, zinc dust (7.27 g, 111 mmol) was added portionwise ensuring the temperature did not exceed 0° C. The suspension was stirred at room temperature for 2 h. The suspension was filtered through celite, extracted with ethyl acetate, washed with 8% sodium bicarbonate, water and brine, dried ($K_2CO_3$), and concentrated to a black oil. Flash chromatography (triethylamine deactivated $SiO_2$, diethylether) gave Intermediate 47, as a red oil (2.9 g, 31%)

T.l.c. $SiO_2$ (Triethylamine deactivated); Diethylether; Rf 0.55.

(b) Dihydro-1-[3-butyloxyphenyl]-1,2,4-triazine-3,5-(2H,4H)-dione

Trifluoroacetic acid (1.2 ml, 15.5 mmol) was added to a suspension of sodium cyanate (1.17 g, 18.0 mmol) and hydrazine (Intermediate 47 1.30 g, 5.15 mmol) in toluene (17 ml) at room temperature and stirred for 2 h. The reaction was quenched with sodium bicarbonate solution, extracted with ethyl acetate and washed with sodium bicarbonate, water and brine, dried ($Na_2SO_4$) and concentrated to afford the urea intermediate as a brown oil. A portion of this crude urea (0.65 g, 2.2 mmol) was taken up in methanol (10 ml) and treated with sodium methoxide (0.48 g, 8.8 mmol) at room temperature for 2 h. The reaction was quenched (pH 6.5 buffer), extracted with ethyl acetate, washed with water followed by brine, dried ($Na_2SO_4$) and concentrated to afford a red oil which was triturated with ether to afford a pale brown solid (105 mg, 18%), m.p. 100°–105°.

T.l.c: Triethylamine deactivated $SiO_2$; EtOAc; Rf 0.45.

EXAMPLE 24

Dihydro-1-(3-phenoxyphenyl)-1,2,4-triazine-3,5-(2H,4H)-dione (a) N-(3-Phenoxyphenyl)glycine methyl ester (Intermediate 48)

A mixture of 3-phenoxyaniline (25 g, 0.135 mol), sodium bicarbonate (22.7 g, 0.27 mol) and methyl chloroacetate (15.5 ml, 0.2025 mol) was heated at 90°–100° C. with vigorous stirring for 20 h. The mixture was allowed to cool to room temperature and was then poured into water (200 ml) and extracted with dichloromethane (2×100 ml). The organic extract was washed with 2N hydrochloric acid (2×100 ml), water (2×100 ml) and then dried and evaporated to give a grey/green solid. This was triturated with hexane (400 ml) and filtered to give the title compound as a grey/green solid (18.4 g, 53%), m.p 44°–45°.

T.l.c.: $SiO_2$; Ether-Hexane (1:1); Rf=0.46.

(b) Methyl [1-(3-phenoxyphenyl)hydrazino]acetate (Intermediate 49)

N-(3-Phenoxyphenyl)glycine methyl ester (Intermediate 48; 10 g, 0.0389 mol) was dissolved in a mixture of glacial acetic acid (60 ml) and water (7 ml) and the solution was cooled to between 0° and 5° C. A solution of sodium nitrite (2.8 g, 0.0408 mol) in water (8.5 ml) was added to this over 15 min at the same low temperature. The solution was stirred for 1 h before being cooled to between 0° and −10° C. Zinc powder (9.9 g, 0.1517 mol) was gradually added at this temperature and the reaction was then stirred at 0° to 5° C. for 4 h. It was then poured into water (300 ml) and extracted with ethyl acetate (3×150 ml). The organic extract was washed with 8% sodium bicarbonate solution until effervescence had ceased. It was then dried and evaporated to give a dark brown oil. This was purified by FCC on deactivated silica (200 g) eluting with hexane-chloroform (2:1) to give the title compound as a brown oil (2.7 g, 25%).

T.l.c: $SiO_2$; Ether-Hexane (1:1); Rf 0.31.

(c) Dihydro-1-(3-phenoxyphenyl)-1,2,4-triazine-3,5-(2H,4H)-dione

A mixture of methyl [1-(3-phenoxyphenyl)hydrazino]acetate (Intermediate 49; 1 g, 0.0037 mol), sodium cyanate (0.82 g, 0.0126 mol) and trifluoroacetic acid (0.88 ml, 0.0114 mol) in toluene (20 ml) was stirred at room temperature and under nitrogen for 3 h. It was then poured into 8% sodium bicarbonate (50 ml) and extracted with ethyl acetate (3×75 ml). The organic extract was dried and evaporated to a pale yellow oil.

This was dissolved in methanol (15 ml) and sodium methoxide solution (1.7 ml, 0.0114 mol: 2.17 molar strength) was added. The mixture was stirred for 5–10 min then poured into pH 6 buffer (75 ml) and extracted with ethyl acetate (3×75 ml). The organic extract was dried and evaporated to give a brown oil which was triturated with ether and filtered to give the title compound as a white solid (114 mg, 11%); m.p. 172°–173°.

T.l.c.: $SiO_2$; Ether; Rf 0.54.

EXAMPLE 25

Dihydro-1-[3-(2-methoxyethoxy)phenyl]-1,2,4-triazine-3,5-(2H,4H)-dione (a) 3-(2-Methoxyethoxy)nitrobenzene (Intermediate 50)

3-Nitrophenol (25 g, 0.18 mol), 2-bromoethyl methyl ether (17 ml, 25 g, 0.18 mol) potassium carbonate (25.0 g, 0.18 mol) in acetone (150 ml) were heated under reflux for 72 h. The suspension was dissolved in water and extracted with ether. The extracts were washed with 2N sodium carbonate, water and saturated brine, dried ($K_2CO_3$), and concentrated, to give the title compound (Intermediate 50) as a brown oil (35.12 g, 99%).

T.l.c: Triethylamine deactivated $SiO_2$; $Et_2O$; Rf 0.5.

(b) 3-(2-Methoxyethoxy)aniline hydrochloride (Intermediate 51)

Palladium on charcoal (0.94 g) and Intermediate 50 (35.0 g, 177 mmol) in ethanol (250 ml) were stirred under a hydrogen atmosphere for 30 min. When the suspension had taken up the calculated amount of hydrogen (8.5 l), the suspension was filtered and the filtrate evaporated to give the free base of the title compound. A portion of the yellow oil (7.83 g, 26%) was used to prepare Intermediate 52, the remainder was converted to the title compound (Intermediate 51) (23.08 g, 64%) with concentrated hydrochloric acid, and triturated with ethyl acetate to afford a grey/white solid m.p. 100°–102° C.

(c) N-[3-(2-Methoxyethoxy)phenyl]glycine, methyl ester (Intermediate 52)

Methyl chloroacetate (6.2 ml, 70.3 mmol), the free base of Intermediate 51 (7.84 g, 46.9 mmol) and sodium hydrogencarbonate (7.9 g 93.8 mmol) were heated at 100° C. for 24 h. The reaction was cooled, extracted with ethyl acetate, washed with water, 2N hydrochloric acid and brine, dried ($K_2CO_3$) and evaporated to give the title compound (Intermediate 52; 11.03 g, 98%) as a brown oil.

Analysis Found: C,60.00; H,7.13; N,5.77. $C_{12}H_{17}NO_4$ Requires C,60.24; H,7.16: N,5.85%.

(d) Methyl (2-[3-(2-methoxyethoxy)phenyl]hydrazino)acetate (Intermediate 53)

Sodium nitrite (7.0 g, 98 mmol) in water (20 ml) was added dropwise to a solution of glycine (Intermediate 52; 22.3 g, 93 mmol) in acetic acid (100 ml) at −5° C. The temperature did not rise above 0° C. The solution was stirred at −5° C. for 1 h. Zinc dust (24.0 g, 373 mmol) was added portionwise. The temperature did not rise above +5° C. After stirring for 2 h the reaction was filtered through celite, extracted with ethyl acetate, washed with sodium bicarbonate, water and brine, dried ($K_2CO_3$) and then concentrated to black oil. Flash chromatography (Triethylamine deactivated. $SiO_2$; using dichloromethane as eluent and then 5% methanol in dichloromethane afforded the desired Intermediate 53 as a black oil (11.0 g, 46%)

T.l.c: Triethylamine deactivated $SiO_2$; 5% methanol in dichloromethane; Rf 0.35.

(e) Dihydro-1-[3-(2-methoxyethoxy)phenyl]-1,2,4-triazine-3,5-(2H,4H)-dione

Trifluoroacetic acid (5.0 ml, 65 mmol) was added to a suspension of sodium cyanate (5.0 g, 76.7 mmol), and hydrazine (Intermediate 53; 5.79 g, 21.9 mmol) in toluene (50 ml). After stirring for 2 h the black slurry was quenched with 8% sodium bicarbonate extracted with ethyl acetate and washed with sodium bicarbonate, water and brine, dried ($Na_2SO_4$) and concentrated to a black oil which was used crude in the next stage.

A portion of crude urea (3.76 g, 12.6 mmol) was taken up in methanol (13 ml) and sodium methoxide (1.36 g, 25.2 mmol) was added, the reaction was stirred at room temperature for 2 h. The reaction was quenched (pH 6.5 buffer), extracted with ethyl acetate, washed with water and brine, dried ($Na_2SO_4$) and concentrated to a brown oil. Flash chromatography (triethylamine deactivated $SiO_2$; ethyl acetate) afforded a yellow solid which was triturated with ether to give a pale tan compound.

Recrystallisation from ethyl acetate gave a pale tan compound (67 mg, 1%) m.p 125°–8° C.

T.l.c. Triethylamine deactivated $SiO_2$; Ethyl acetate; Rf 0.45.

EXAMPLE 26

Dihydro-1-[3-(monofluoromethyl)phenyl]-1,2,4-triazine-3,5-(2H,4H)-dione

(a) N-[3-(Fluoromethyl)phenyl]glycine methyl ester (Intermediate 54)

3-Fluoromethyl aniline (containing 37% 3-methylaniline, 13.6 g≡68 mmol) was mixed with dry acetonitrite (10 ml), sodium bicarbonate (15.4 g, 183 mmol) and methyl chloroacetate (12 ml, 137 mmol) and heated to 90° C. under nitrogen for 14 h. The cooled reaction mixture was poured into water (100 ml) and extracted with ethyl acetate (4×100 ml). The combined organic extracts were dried ($Na_2SO_4$) and concentrated in vacuo to give an orange oil. The crude product was purified by chromatography on silica (Merck 9385, 1.5 kg) eluted with ether-hexane 1:4 to give Intermediate 54 (6.45 g, 48%) as a white crystalline solid, m.p. 47°–47.5°.

T.l.c $SiO_2$, Ether-hexane (1:1), Rf 0.34

(b) Methyl [1-[3-(Fluoromethyl)phenyl]hydrazino]acetate (Intermediate 55)

The glycine (Intermediate 54, 1 g, 5.1 mmol) was dissolved in acetic acid (10 ml) and water (1 ml) and cooled to ~5° C. Sodium nitrite (0.37 g, 5.4 mmol) in water (1.3 ml) was added to the glycine solution dropwise, maintaining the temperature at or below 5° C. The reaction was stirred at this temperature for 1 h. Zinc (1.33 g, 20.3 mmol) was then added slowly to the reaction keeping the temperature below 4° C., and the reaction was stirred for 1 h. The reaction mixture was poured into water (100 ml) and extracted with ethyl acetate (3×100 ml). The combined organic extracts were washed with water (2×100 ml) followed by saturated aqueous sodium bicarbonate (1×100 ml) then water (100 ml), dried ($Na_2SO_4$) and concentrated in vacuo to give an orange oil (1.06 g). The crude material was purified by chromatography on silica (Merck 9385, 28 g) eluted with ether-hexane 1:4 to give the title compound (Intermediate 55, 453 mg, 40%).

T.l.c $SiO_2$, ether-hexane (1:1) Rf 0.07.

(c) Methyl [2-Aminocarbonyl)-1-[3-(fluoromethyl)phenyl]hydrazino]acetate (Intermediate 56)

The hydrazine (Intermediate 55, 1.5 g, 7.1 mmol) was dissolved in dry toluene (30 ml) under nitrogen at room temperature. Sodium cyanate (1.6 g, 24.6 mmol) was added followed by trifluoroacetic acid (1.7 ml, 22,1 mmol). The reaction was stirred for 2.25 h after which the reaction was poured into saturated sodium bicarbonate solution (100 ml) and extracted with ethyl acetate (4×(100 ml). The combined extracts were dried ($Na_2SO_4$) and concentrated in vacuo to give a white solid. The crude material was triturated with ether (2×100 ml) to give the title compound (Intermediate 56, 1.41 g, 78%) as a colourless powder, m.p. 169°–70°.

T.l.c $SiO_2$ ETOAc, Rf 0.14.

(d) Dihydro-1-[3-(Fluoromethyl)phenyl]1,2,4-triazine-3,5(2H,4H)dione

The urea (Intermediate 56, 0.8 g, 3.1 mmol) was suspended in dry methanol (20 ml) under nitrogen at room temperature. Solid sodium methoxide (340 mg, 6.3 mmol) was added in one portion. After ten minutes the urea dissolved to give a yellow solution. The reaction was stirred at room temperature for 1 h, was then poured into pH6.5 phosphate buffer solution (60 ml) and extracted with ethyl acetate (4×30 ml). The combined organic extracts were dried ($Na_2SO_4$) and concentrated in vacuo to give a pale yellow solid. The crude material was triturated with ether (4×50 ml) and dried in vacuo to give the title compound (310 mg, 44%) as a colourless solid, m.p. >300°.

T.l.c, SiO$_2$, Ethyl acetate, Rf 0.64.

EXAMPLE 27

Dihydro-1-(4-bromophenyl)-1,2,4-triazine-3,5-(2H,4H)-dione (a) N-(4-Bromophenyl)glycine, methyl ester (Intermediate 57)

The p-bromoaniline (25 g, 0.145 mol), sodium bicarbonate (24.4 g, 0.29 mol) and methyl chloroacetate (14 ml, 0.16 mol) were allowed to reflux at 130° C. for 48 h. The mixture was cooled before treating with 2N HCl and extracting with ether. The ether extracts were washed with water, brine and dried (Na$_2$SO$_4$). Filtration and evaporation gave a solid. Trituration with ether followed by recrystallisation from EtOAc/hexane gave the glycine (Intermediate 57, 6.94 g, 20%) M.p. decomposes >110° C.

(b) Methyl [1-[4-bromophenyl]hydrazino]acetate (Intermediate 58)

A solution of sodium nitrite (5.41 g, 0.078 mol) in water (10 ml) was added to the glycine, (Intermediate 57, 17.4 g, 0.071 mol) in acetic acid (50 ml) whilst keeping the temperature below 0° C. After 0.5 h zinc dust (5.13 g, 0.078 mol) was added portionwise keeping the temperature below 5° C. A further amount of zinc (10.2 g, 0.156 mol) was then added and the mixture left overnight. The solution was neutralized with bicarbonate and extracted with EtOAc. The extracts were washed with water and brine and then dried (Na$_2$SO$_4$). The solution was filtered, evaporated and then chromatographed using 30% ether/hexane to give the hydrazine (Intermediate 58, 6.0 g, 32%).

T.l.c. SiO$_2$, 1:1 ether/hexane, Rf 0.25.

(c) Methyl [2-(aminocarbonyl)-1-(4-bromophenyl)hydrazino]acetate (Intermediate 59)

To the hydrazino (Intermediate 58, 6.0 g, 24.5 mmol) and sodium cyanate (4.95 g, 76.2 mmol) in toluene (30 ml) was added trifluoroacetic acid dropwise (5.68 ml, 74 mmol). The mixture was left to stir for 5 minutes. The reaction was quenched with NaHCO$_3$ and extracted with EtOAc. The organic extracts were washed with water and brine and then dried (Na$_2$SO$_4$). Filtration and evaporation followed by trituration with ether gave the urea (Intermediate 59) as a cream solid (4.416 g, 63%.)

T.l.c SiO$_2$, 1:1 THF/hexane, Rf 0.06.
M.p. 117.5°–122.5° C.

(d) Dihydro-1-(4-bromophenyl)-1,2,4-triazine-3,5(2H,4H)-dione

The urea, (Intermediate 59, 2.26 g, 7.5 mmol) and sodium methoxide (525 mg; 9.7 mmol) were stirred under nitrogen in methanol (20 ml) for 2 h. A further amount of sodium methoxide (100 mg; 1.9 mmol) was added and the reaction left overnight. The reaction was neutralised with acid (2N HCl) and the precipitate was filtered. The precipitate was recrystallised several times from dioxan to give the title compound (357 mg; 18%).

T.l.c. SiO$_2$, 5% MeOH/CHCl$_3$ Rf 0.58.
M.p >190° C. (dec.).

EXAMPLE 28

Dihydro-1-(4-ethylphenyl)-1,2,4-triazine-3,5-(2H,4H)-dione (a) N-(4-(Ethylphenyl))glycine, methyl ester (Intermediate 60)

p-Ethylaniline (25 g, 0.206 mol), sodium bicarbonate (34.66 g, 0.412 mol) and methylchloroacetate (19.9 ml, 0.227 ml) were allowed to reflux at 130° for 72 h. The mixture was then cooled before being quenched with dilute HCl and extracted with ether. The ether extracts were washed with water and brine and then dried (Na$_2$SO$_4$). Filtration and evaporation gave the glycine, (Intermediate 60, 33.3 g, 84%) as an oil.

T.l.c. Ether on SiO$_2$ Rf 0.62.

(b) Methyl [1-[4-ethylphenyl]hydrazino]acetate (Intermediate 61)

A solution of sodium nitrite (13.23 g, 0.1917 mol) in water (10 ml) was added dropwise to the glycine, (Intermediate 60, 33.1 g, 0.171 mol) in acetic acid (50 ml), ensuring the temperature did not rise above 0° C. This was left to stir for 0.5 h. Then zinc dust (12.54 g, 0.1918 mol) was added portionwise, not allowing the temperature to exceed 5° C. After 2 h, a second amount of zinc dust (12.54 g, 0.1918 mol) was added. After 4 h, a final amount of zinc (12.54 g, 0.1918 mol) was added and the reaction was left overnight. Excess zinc was removed by filtration. Then the solution was neutralized with bicarbonate solution and extracted with EtOAc. The organic extracts were washed with water and brine and then dried (Na$_2$SO$_4$). Filtration and evaporation gave an oil. The oil was chromatographed using 50% ether/hexane to give the hydrazine (intermediate 61, 6.10 g, 14%).

T.l.c. Ether/hexane (1:1) on SiO$_2$, Rf 0.58.

(c) Methyl [2-(aminocarbonyl)-1-(4-ethylphenyl)hydrazino]acetate (Intermediate 62)

Trifluoroacetic acid (6.55 ml, 85 mmol) was added dropwise to a solution of the hydrazine (Intermediate 61, 6.0 g, 28.8 mmol) and sodium cyanate (5.618 g, 86.4 mmol) in toluene (40 ml). This reaction mixture was left for 3 h. The reaction was then quenched with NaHCO$_3$ and extracted with EtOAc. The organic extracts were washed with water and brine and then dried (Na$_2$SO$_4$). Filtration and evaporation gave a cream solid. This was triturated with ether to give the urea (Intermediate 62) as a white solid (4.54 g, 63%)

T.l.c. SiO$_2$ 5% MeOH/CH$_2$Cl$_2$; Rf 0.38.
M.p. 140°–142° C.

(d) Dihydro-1-(4-ethylphenyl)-1,2,4-triazine-3,5(2H,4H)-dione

The urea (Intermediate 62 2.2 g, 8.6 mmol) and sodium methoxide (567 mg, 10.5 mmol) were stirred in methanol (10 ml) for 3 h. After this time, a second amount of methoxide (100 mg, 1.9 mmol) was added and the reaction was left to stir for 2 h. The reaction mixture was then quenched with 2N HCl to pH7. The solid formed was filtered, and then recrystallised (methanol/dioxan) to give the title compound (563 mg, 29%)

T.l.c. SiO$_2$, THF/hexane (1:1); Rf 0.60.
M.p. >175° C.(dec).

EXAMPLE 29

Dihydro-1-(4-fluoro-3-methylphenyl)-1,2,4-triazine-3,5-(2H,4H)-dione

(a) N-(4-Fluoro-3-methylphenyl)glycine methyl ester (Intermediate 63)

A mixture of 4-fluoro-3-methylaniline (20 g, 0.1599 mol), sodium bicarbonate (26.9 g, 0.3198 mol) and methyl chloroacetate (21 ml, 0.2399 mol) was heated at 90°-100° C. with rigorous stirring for 24 hours. The mixture was allowed to cool to room temperature and then poured into water (200 ml). The mixture was extracted with ethyl acetate (2×100 ml) and the extracts were dried (MgSO$_4$) and evaporated to give an off white solid. This was triturated to give an impure pale grey solid (17.2 g, 55%). The title compound (Intermediate 63) was obtained by recrystallisation with hexane (150 ml) giving a pale brown solid (7.6 g, 24%), m.p. 74°-75° C.

T.l.c. Ether on SiO$_2$, Rf 0.74.

(b) Methyl [1-[4-fluoro-3-methylphenyl]hydrazino]acetate (Intermediate 64)

N-(4-Fluoro-3-methylphenyl)glycine methyl ester (Intermediate 63, 7.5 g, 0.038 mol) was dissolved in a mixture of glacial acetic acid (60 ml) and water (8 ml) and the solution was cooled to ~5° C. To this was added a solution of sodium nitrite (4.3 g, 0.063 mol) in water (15 ml) at the same low temperature over 20 minutes. Stirring was continued for 1 hour and the temperature was then lowered to between −10° and 0° C. Zinc dust (15.3 g, 0.234 mol) was added at the maintained low temperature and the resulting suspension was stirred at ~0° C. for 4 hours. It was then poured into water (250 ml) and extracted with ethyl acetate (2×200 ml). The extract was washed with 8% sodium bicarbonate solution until all effervescence had ceased. It was then dried (MgSO$_4$) and evaporated to give a brown semi-solid. This was triturated with ether/hexane (1:2, ~15 ml) to give a white solid which was filtered and washed with ice-cold ether. The liquors were evaporated to give a brown oil and this was purified by flash column chromatography on silica (Merck 9385; 225 g) eluting with ether/hexane (1:1) to give the title compound (Intermediate 64) as an orange oil (1.4 g, 17%).

T.l.c. SiO$_2$, Ether-hexane (1:1), Rf 0.24.

(c) Methyl [2-(aminocarbonyl)-1-(4-fluoro-3-methylphenyl)hydrazino]acetate (Intermediate 65)

A mixture of methyl [1-(4-fluoro-3-methylphenyl)hydrazino]acetate (Intermediate 64, 0.8, 38 mml), sodium cyanate (0.84 g, 0.0129 mol) and trifluoroacetic acid (0.95 ml, 0.0114 mol) in toluene (15 ml) was stirred under nitrogen at room temperature for 24 hours. The mixture was poured into 8% sodium bicarbonate solution (40 ml) and extracted with ethyl acetate (2×30 ml). The organic extract was dried (MgSO$_4$) and evaporated to give a red oil. This was crystallised by trituration with ether to give a white solid (Intermediate 65, 228 mg; 24%), m.p. 132°-133° C.

T.l.c. Ether on SiO$_2$, Rf 0.45.

(d) Dihydro-1-(4-fluoro-3-methylphenyl)-1,2,4-triazine-3,5-(2H,4H)-dione

To a solution of methyl [2-(aminocarbonyl)-1-(4-fluoro-3-methylphenyl)hydrazino]acetate (Intermediate 65, 1 g, 0.0039 mol) in methanol (35 ml) was added sodium methoxide (0.21 g, 0.0039 mol). The mixture was stirred for 1.5 hours and then poured into pH6 buffer (100 ml). This was extracted with ethyl acetate (75 ml) and the extract was dried (MgSO$_4$) and evaporated to give a white solid. This was triturated with ether and filtered to give a white solid (0.359 g, 41%). This solid was recrystallised in ethyl acetate-ether to give the title compound as a white solid (181 mg, 21%), m.p. 211°-213° C.

T.l.c. Ethyl acetate on SiO$_2$, Rf 0.78.

EXAMPLE 30

Dihydro-1-[3-(hexyloxy)phenyl]-1,2,4-triazine-3,5-(2H,4H)-dione

(a) 1-(Hexyloxy)-3-nitrobenzene (Intermediate 66)

A mixture of 3-nitrophenol (57.0 g, 0.41 mol), n-hexyliodide (87.0 g, 0.41 mol), potassium carbonate (57.0 g, 0.42 mol) and ethylmethylketone (300 ml) was heated at reflux for 18 h. Water (500 ml) was added and the mixture was extracted with ethyl acetate (2×500 ml). The combined extracts were washed with 8% aqueous sodium bicarbonate (2×250 ml) and brine (250 ml) and then dried (MgSO$_4$) and evaporated to afford a dark brown liquid. Distillation under reduced pressure gave the ether (Intermediate 66) as a mobile yellow liquid (70.3 g, 77%).

B.p. 109°-113° C. @0.19 mmHg.

(b) 3-(Hexyloxy)aniline (Intermediate 67)

1-(Hexyloxy)-3-nitrobenzene (Intermediate 66, 70.0 g, 0.31 mol) in ethanol (500 ml) and 5% platinum on carbon (1.5 g) were vigorously agitated under a hydrogen atmosphere. Rapid uptake of hydrogen occurred, ceasing when 22.41 (ca. 3 eq.) had been consumed. The catalyst was removed by filtration and the filtrate was evaporated to afford a light yellow oil. Hexane (50 ml) was added and the resultant solution was then cooled in dry ice, causing the aniline to crystallise. Removal of the hexane by evaporation afforded the aniline (Intermediate 67) as a white solid (59.0 g, 98.5%).

(c) N-(3-Hexyloxyphenyl)glycine methyl ester (Intermediate 68)

A mixture of the aniline (Intermediate 67, 38.7 g, 0.20 mol), sodium hydrogen carbonate (33.6 g, 0.51 mol) and ethyl chloroacetate (26.4 ml, 0.24 mol) was rapidly stirred and heated at ca. 90° C. for ca. 18 h. Water (250 ml) was added and the mixture was extracted with ethyl acetate (2×250 ml). The combined extracts were washed with water (100 ml) and brine (100 ml) and then dried (MgSO$_4$) and evaporated to afford a red oil (49 g). Flash column chromatography on silica gel (Merck 9385, 750 g), hexane/ether (2:1) as eluent, afforded the glycine (Intermediate 68) as an orange oil, slightly contaminated with aniline. Trituration with hexane (30 ml) gave the pure glycine as a white solid (26.2 g, 49%), m.p. 35° C.

T.l.c. hexane/ether (1:1) on SiO$_2$; Rf 0.56

(d) Methyl [1-[3-(hexyloxy)phenyl]hydrazino]acetate (Intermediate 69)

A solution of sodium nitrite (4.34 g, 0.063 mol) in water (15 ml) was added dropwise to a stirred solution of the glycine (Intermediate 68, 16.0 g, 0.060 mol) in glacial acetic acid (100 ml) and water (10 ml) at 5°–10° C. On completion of the addition, the resultant dark brown solution was stirred at room temperature for a further hour. It was cooled to ca. 5° C. and zinc powder (15.6 g, 0.23 mol) was cautiously added at such a rate that the temperature did not rise above 20° C. Ethyl acetate (250 ml) was added, the mixture was filtered, and the filtrate was washed with water (3×250 ml). Residual acetic acid was neutralized by addition of solid sodium hydrogen carbonate until effervesence ceased. The mixture was washed again with water (250 ml), dried (MgSO$_4$) and evaporated to yield a brown oil (15.0 g). Flash column chromatography on silica gel (Merck 9385, 700 g), hexane/ether (2:1) as the eluent, gave the hydrazine (Intermediate 69) as a brown oil (4.80 g, 28%).

Trituration with hexane (15 ml) gave the hydrazine as a white solid (4.1 g, 24%); m.p. 40°–42° C.

T.l.c SiO$_2$, Hexane/ether (1:1), Rf 0.25.

(e) Methyl [2-aminocarbonyl-1-[3-(hexyloxy)phenyl]hydrazino]acetate (Intermediate 70)

Trifluoroacetic acid (2.35 ml, 31 mmol) was added, under nitrogen, to a stirred suspension of sodium cyanate (2.24 g, 34 mmol) in a solution of the hydrazine (Intermediate 69, 3.00 g, 10.7 mmol) in toluene (50 ml). After stirring for ca. 4 h, 8% w/v aqueous sodium hydrogen carbonate (50 ml) was added and the mixture was extracted with ethyl acetate (3×50 ml). The combined extracts were washed with brine (50 ml), dried (MgSO$_4$), and evaporated to afford a viscous yellow oil. Trituration with hexane/ether (1:1) (25 ml) gave the urea (Intermediate 70) as a white powder (2.65 g, 77%), m.p. 97°–98° C.

(f) Dihydro-1-[3-(hexyloxy)phenyl]-1,2,4-triazine-3,5-(2H,4H)-dione

Sodium methoxide (0.33 g, 6.2 mmol) was added under nitrogen to a stirred solution of the urea (Intermediate 70, 1.00 g, 3.1 mmol) in 1,2-dimethoxyethane (25 ml) over 4 A° molecular sieves. After 15 minutes the mixture was poured into pH6.5 aqueous phosphate buffer (100 ml) and extracted with ethyl acetate (3×100 ml). The combined extracts were dried (MgSO$_4$) and evaporated to afford the crude product as an off-white solid. Trituration with hexane/ether (ca. 1:2) (25 ml) gave the title compound as a white powder (600 mg, 67%) m.p. 161°–163° C.

T.l.c. SiO$_2$, ethyl acetate, Rf 0.65.

EXAMPLE 31

Dihydro-1-[3-(3-ethoxypropoxy)phenyl]-1,2,4-triazine-3,5-(2H,4H)-dione

(a) 3-(3-ethoxypropoxy)nitrobenzene (Intermediate 71)

3-Ethoxypropyl chloride (30.0 g, 0.24 mole) was added to a solution of 3-nitrophenol (33.4 g, 0.24 mole) in acetone (500 ml), and heated under reflux for 7 days. Sodium iodide (36.7 g, 0.24 mole) and dimethylformamide (200 ml) were then added and the whole was heated under reflux for a further 3 days. The acetone was then distilled off and the cooled solution was quenched (H$_2$O), extracted (EtOAc), washed (Na$_2$CO$_3$/NaCl), dried, and concentrated.

T.l.c SiO$_2$, Ether/Hexane (1:1), Rf 0.70

(b) N-[3-(3-ethoxypropoxyphenyl]glycine, methyl ester (Intermediate 72)

The alkoxynitrobenzene (Intermediate 71, 0.202 mole) in methanol (300 ml), with 5% platinum on carbon (2.0 g) as catalyst, was stirred vigorously under a hydrogen atmosphere until hydrogen consumption ceased (1 h). Degassing and filtration through celite afforded the aniline as an unstable brown oil. The aniline (0.202 mole), methyl chloroacetate (17.7 ml, 0.202 mole) and sodium hydrogen carbonate (20.36 g, 0.242 mole) were then heated at 100° C. for 24 h. After this time, the reaction mixture was cooled, taken up in ethyl acetate, washed (H$_2$O, sat. NaCl soln.) dried (MgSO$_4$) and concentrated to afford the glycine (Intermediate 72) as a brown oil. A portion of the glycine was purified by flash chromatography (SiO$_2$, ether hexane (1:1) to afford the title compound as a yellow oil, which solidified on standing as colourless prisms, m.p. 62° C.

T.l.c. SiO$_2$, ether/hexane, (1:1) Rf 0.30.

(c) Methyl [1-[3-(3-ethoxypropoxy)phenyl]hydrazino]-acetate (Intermediate 73)

Sodium nitrite (15.33 g, 0.22 mol) in water (20 ml) was added dropwise to a solution of the glycine (Intermediate 72, 0.202 mol) in acetic acid (200 ml) and methanol (20 ml) ensuring the temperature remained below 0° C. Zinc (31.6 g, 0.48 mol) was then cautiously added to the 0° C. solution ensuring the temperature did not rise above 5° C. The reaction was neutralised (2M NaOH), extracted (EtOAc), washed (H$_2$O, sat. NaCl soln), dried (Na$_2$SO$_4$), and concentrated. Flash chromatography of the residue (SiO$_2$, (1:1) ether:hexane then 100% ether) afforded the title compound as a red oil (8.94 g, 16%).

T.l.c. SiO$_2$, (1:1) ether:hexane, Rf 0.05.

(d) Methyl[2-aminocarbonyl-1-[3-(3-ethoxypropoxy)-phenyl)]hydrazino]acetate (Intermediate 74)

Trifluoroacetic acid (7.32 ml, 95 mmol) was added dropwise to a suspension of the hydrazine (Intermediate 73, 8.94 g, 31.7 mmol) and sodium cyanate (7.21 g, 11 mmol) in toluene (63 ml) at room temperature. After stirring for 30 min the mixture was taken up in chloroform, quenched (NaHCO$_3$), extracted (CHCl$_3$), washed (H$_2$O, sat. NaCl), dried (Na$_2$SO$_4$) and concentrated. The residue was subjected to column chromatography (SiO$_2$, 10% MeOH in CHCl$_3$) to afford the title compound as a pale yellow glass (6.78 g, 66%).

T.l.c. SiO$_2$, 10% MeOH in CHCl$_3$ Rf 0.40.

(e) Dihydro-1-[3-(3-ethoxypropoxy)phenyl]-1,2,4-triazine-3,5-(2H,4H)-dione

Sodium methoxide (1.67 g, 30.9 mmol) was added to a solution of the urea (Intermediate 74, 6.78 g, 20.8 mmol) in methanol (30 ml) and stirred at room temperature for 30 min. The reaction mixture was poured into water, neutralised (2N HCl) and cooled. The solid was filtered, washed (H$_2$O) and dried to afford the title compound as an off-white solid (4.31 g, 71%). A sample was recrystallised from methanol, m.p. 137° C. T.l.c. SiO$_2$, EtOAc, Rf 0.75.

EXAMPLE 32

Dihydro-1-(4-phenoxyphenyl)-1,2,4-triazine-3,5-(2H,4H)-dione

(a) N-(4-Phenoxyphenyl)glycine, methyl ester (Intermediate 75)

A mixture of 4-phenoxyaniline (30 g, 0.162 mol), methyl chloroacetate (21.3 ml, 0.243 mol) and sodium bicarbonate (27.2 g, 0.324 mol) was heated at 100°–120° C. with magnetic stirring for 24 hours. The resulting semi-solid was partitioned between dichloromethane (300 ml) and water (300 ml) then separated. The aqueous layer was extracted with dichloromethane (200 ml) and the organic extracts were combined. The extracts were washed with 2N hydrochloric acid (2×200 ml) and water (2×200 ml), dried (MgSO$_4$) and evaporated to give a brown oil. This was heated with hexane (300 ml) to give an oil suspension. The hexane was decanted off and residual oil crystallised on cooling. The solid was triturated with ether/hexane 1:1 and filtered to give a brown solid (13.6 g, 33%) m.p. 80°–82° C. A second crop of a pale yellow solid was also given (10.5 g, 25%).

T.l.c. Ether-hexane (1:1) on SiO$_2$ Rf 0.45.

(b) Methyl [1-(4-phenoxyphenyl)hydrazino]acetate (Intermediate 76)

N-(4-Phenoxyphenyl)glycine methylester (Intermediate 75, 13.5 g, 0.0525 mol) was dissolved in a mixture of acetic acid (90 ml) and water (5 ml) and the solution was cooled to ~5° C. To this was added a solution of sodium nitrite (3,8 g, 0.55 mol) in water (10 ml) over 15 minutes. Stirring was continued for 2 hours and the reaction was cooled to ~0° C. Zinc dust (13.4 g, 0.2048 mol) was added over 30 minutes and the reaction stirred at 0°–5° C. for 2 hours before being poured into water (200 ml) and extracted with ethyl acetate (2×150 ml). The organic extract was washed with 8% sodium bicarbonate solution until effervescence had ceased, dried (MgSO$_4$) and evaporated to give a brown semi-solid. This was triturated with ether/hexane (1:1) to recover starting material (6.5 g, 48%). The liquors were evaporated and purified by flash column chromatography on silica (Merck 9385; 250 g) eluting with ether-hexane (1:1) to give the title compound (Intermediate 76) as an off white solid (1.25 g, 9%) m.p 71°–73° C.

T.l.c. Ether-hexane (1:1) on SiO$_2$ Rf 0.21.

(c) Methyl [2-(aminocarbonyl)-1-(4-phenoxyphenyl)hydrazino]acetate (Intermediate 77)

A mixture of methyl [1-[4-phenoxyphenyl]hydrazino]acetate (Intermediate 76, 11 g, 0.004 mol), sodium cyanate (0.9 g, 0136 mol) and trifluoroacetic acid (1 ml, 0.0124 mol) in dry toluene (15 ml) was stirred under nitrogen at room temperature for 1 hour. The mixture was poured into 8% sodium bicarbonate solution (75 ml) and extracted with ethyl acetate (2×75 ml). The organic extract was dried (MgSO$_4$) and evaporated to give a pale yellow semi-solid. This was triturated with ether to give the title compound (Intermediate 77) as a white solid (0.6 g, 48%) m.p. 110°–113° C.

T.l.c Ethyl acetate on SiO$_2$ Rf 0.35.

(d) Dihydro-1-(4-phenoxyphenyl)-1,2,4-triazine-3,5-(2H,4H)-dione

To a solution of methyl [2-(aminocarbonyl)-1-(4-phenoxyphenyl)hydrazino]acetate (Intermediate 77, 550 mg, 0.0017 mol) in methanol (20 ml) was added sodium methoxide (184 mg, 0.0014 mol) and the mixture was stirred for 2 hours then poured into pH6 buffer (70 ml). This was extracted with ethyl acetate (75 ml), dried (MgSO$_4$) and evaporated to give an off-white solid. This was triturated with ethyl acetate-ether and filtered to give the title compound as an off-white solid (90 mg, 19%) m.p. 211°–213° (dec).

T.l.c. Ethyl acetate on SiO$_2$, Rf 0.77.

EXAMPLE 33

Dihydro-1-[3-(4-fluorophenylmethoxy)phenyl]-1,2,4-triazine-3,5-(2H,4H)-dione

(a) N-[3-(4-Fluorophenylmethoxy)phenyl]glycine, methyl ester (Intermediate 78)

A mixture of 3-(4-fluorophenylmethoxy) aniline hydrochloride (30 g, 0.118 mol), sodium bicarbonate (29.7 g, 0.354 mol) and methyl chloroacetate (15.5 ml, 0.177 mol) in acetonitrile (50 ml) was heated at 90° for 48 h.

Water (200 ml) was added and the mixture was extracted with ethyl acetate (2×200 ml). The combined extracts were washed with water (2×200 ml) and brine (200 ml) before drying (Na$_2$SO$_4$) and evaporation in vacuo to give a brownish semi-solid. On trituration with ether-hexane (1:1), the brown semi-solid gave the title compound as a grey solid (24.1 g; 70.6%) m.p. 73°–75°.

T.l.c. SiO$_2$, ether-hexane (1:1), Rf 0.48.

(b) Methyl[1-[3-(4-fluorophenylmethoxy)phenyl]hydrazino)acetate (Intermediate 79)

Sodium nitrite (6.03 g, 87.5 mmol) in water (50 ml) was added dropwise over 0.5 h to a stirred solution of the glycine (Intermediate 78, 23 g, 79.5 mmol) in glacial acetic acid (200 ml) and methanol (50 ml) at 0°–5°. The deep orange solution was then held at ≦0° for 1.5 h before cooling to −10°.

Zinc dust (18.1 g, 277 mmol) was added over 0.5 h at <0° and the mixture was stirred at ≦0° for a further 3 h. Water (200 ml) was added and the mixture was extracted with ethyl acetate (2×200 ml). The combined extracts were washed with 8% sodium bicarbonate (4×200 ml), water (2×100 ml) and brine (200 ml) before drying and evaporating to a brown oil (14.3 g).

Column chromatography on triethylamine deactivated silica (Merck 9385, 500 g) eluting with ether-hexane (1:1) gave the title compound as an orange solid (3.9 g; 16.1%), m.p. 75°–77°.

T.l.c. SiO$_2$ (NEt$_3$ deactivated), ether/hexane (1:1), Rf 0.12.

(c) Methyl [2-(aminocarbonyl)-1-[3-(4-fluorophenylmethoxy)phenyl]hydrazino]acetate (Intermediate 80)

Trifluoroacetic acid (2.75 ml, 35.8 mmol) was added at 25° to a stirred suspension of the hydrazine (Intermediate 79, 3.7 g, 12.2 mmol) and sodium cyanate (2.71 g, 41.75 mmol) in toluene (70 ml). The mixture was stirred at 25° for 1 h, during which time a white solid precipitated. 8% sodium bicarbonate (100 ml) was added and the mixture was extracted with ethyl acetate (2×100 ml). The combined extracts were then washed with water (2×100 ml) and brine (100 ml) before drying (Na₂SO₄) and evaporating in vacuo to a yellow oil. Trituration with hexane/ether/ethyl acetate (1:1:4) gave the title compound (Intermediate 80) as a white crystalline solid (2.9 g; 68%) m.p. 119°–121°.

T.l.c. SiO₂, ethyl acetate, Rf 0.28.

(d) Dihydro-1-[3-(4-fluorophenylmethoxy)phenyl]-1,2,4-triazine-3,5-(2H, 4H)-dione Sodium methoxide (467 mg, 8.6 mmol) was added to a stirred solution of the urea (Intermediate 80, 1 g, 2.88 mmol) in methanol (40 ml) and the mixture was stirred at 20°–25° for 2 h. The mixture was poured into pH6.7 buffer (100 ml) and extracted with ethyl acetate (3×100 ml). The combined extracts were washed with water (2×100 ml) and brine (100 ml) before drying (Na₂SO₄) and evaporating in vacuo to a yellow solid. Trituration with ether gave the title compound as a white solid (265 mg, 29%) m.p. 185°–187° (dec).

T.l.c. SiO₂, ethyl acetate, Rf 0.51.

EXAMPLE 34

Dihydro-1-[3-(4-methylphenylmethoxy)phenyl]-1,2,4-triazine-3,5-(2H,4H)-dione

(a) 3-[4-Methylphenylmethoxy]nitrobenzene (Intermediate 81)

4-Methylbenzylbromide (75 g; 0.405 mol) was added to a stirred suspension of m-nitrophenol (59.1 g, 0.425 mol) and anhydrous potassium carbonate (61.6 g, 0.445 mol) in acetone (500 ml). The mixture was heated under reflux for 4 h.

Potassium bromide was filtered off and the acetone was evaporated to give a red oil. The oil was partitioned between water (200 ml) and ethyl acetate (2×100 ml) and the combined organic extracts were washed with 2N sodium hydroxide (2×100 ml), water (2×100 ml) and brine (100 ml) before drying (Na₂SO₄) and evaporating to give the crude title compound (Intermediate 81), as a yellowish semi-solid. Recrystallisation from ethanol gave the purified product as a cream crystalline solid (90 g, 91.4%), m.p. 58°–59°.

T.l.c. SiO₂, ethyl acetate, Rf 0.77.

(b) 3-[4-Methylphenylmethoxy]benzenamine hydrochloride (Intermediate 82)

The nitrobenzene (Intermediate 81,5 g, 20.1 mmol) was hydrogenated at atmospheric pressure over 5% Platinum oxide on carbon (0.2 g) in ethanol (30 ml) and chloroform (30 ml) for 1.5 h. The catalyst was removed by filtration through hyflo and the solvent was evaporated to a brown oil which on trituration with ether gave a dark grey solid (2.1 g; 41.8%), m.p. 158°–161° (dec).

T.l.c. Triethylamine deactivated SiO₂, Ethyl acetate, Rf 0.67.

(c) N-[3-(4-Methylphenylmethoxy)phenyl]glycine, methyl ester (Intermediate 83)

A mixture of the aniline (Intermediate 82, 20 g, 94 mmol), sodium bicarbonate (11.8 g, 141 mmol) and methyl chloroacetate (9.1 ml, 103 mmol) in acetonitrile (30 ml) was heated at 90°–100° for 24 h. Water (200 ml) was added and the mixture was extracted with ethyl acetate (2×100 ml). The combined extracts were washed with 2N hydrochloric acid (2×100 ml), water (2×100 ml) and brine (100 ml) before drying (Na₂SO₄) and evaporating to an orange solid. Trituration with ether, followed by evaporation of the triturate gave the title compound (Intermediate 83) as a pale grey solid (16 g; 60%), m.p. 78°–80°.

T.l.c. SiO₂, ethyl acetate, Rf 0.70.

(d) Methyl 1-[3-(4-Methylphenylmethoxy)phenyl]hydrazino acetate (Intermediate 84)

Sodium nitrite (4.17 g, 60.5 mmol) in water (40 ml) was added at 0°–5° to a stirred solution of the glycine (Intermediate 83,15.7 g, 55 mmol) in glacial acetic acid (140 ml) and methanol (40 ml). The deep orange mixture was stirred at ≦0° for 1.5 h.

Zinc dust (12.6 g, 192 mmol) was added over 0.5 h at ca −10° causing oiling out of a compound which was slightly redissolved by adding more methanol (75 ml). The mixture was then stirred at ≦0° for 3 h. The zinc residues were filtered, water (400 ml) was added to the filtrate and the mixture was extracted with ethyl acetate (3×100 ml). The combined extracts were washed with 8% sodium bicarbonate solution (4×250 ml), water (2×250 ml) and brine (250 ml) before drying (Na₂SO₄) and evaporating to leave the crude product as a dark brown oil 10.6 g).

Column chromatography on triethylamine deactivated silica (Merck 9385, 500 g) eluting with hexane:ether (1:1) gave the title compound (Intermediate 84) as an orange solid (3.0 g; 18.2%), m.p. 73°–75°.

T.l.c. SiO₂ (NEt₃ deactivated), hexane-ether (1:1), Rf 0.15.

(e) Methyl [2-(aminocarbonyl)-1-[3-(4-methylphenylmethoxy)-phenyl]hydrazino]acetate (Intermediate 85)

Trifluoroacetic acid (2.15 ml, 28 mmol) was added to a stirred suspension of the hydrazine (Intermediate 84, 2.9 g, 9.655 mmol) and sodium cyanate (2.15 g, 33 mmol) in toluene (60 ml). The reddish mixture was stirred at 20°–25° for 1 h, during which time a solid was precipitated.

8% sodium bicarbonate (100 ml) was added and the mixture was extracted with ethyl acetate (2×50 ml). The combined extracts were then washed with water (2×100 ml) and brine (100 ml) before drying (Na₂SO₄) and evaporating in vacuo to a yellow oil. Trituration with ether/ethyl acetate (9:2) gave the title compound (Intermediate 85) as a near white solid (2.1 g; 63%), m.p. 120°–122°.

T.l.c. SiO₂, ethyl acetate, Rf 0.36.

(f) Dihydro-1-[3-(4-Methylphenylmethoxy)phenyl]-1,2,4-triazine-3,5-(2H, 4H)-dione Solid sodium methoxide (236 mg, 4.4 mmol) was added to a stirred solution of the urea (Intermediate 85, 500 mg, 1.5 mmol) in methanol (30 ml). The mixture was stirred at 20°–25° for 2 h. The mixture was then poured into pH6.7 buffer (100 ml) and extracted with ethyl acetate (3×50 ml). The combined extracts were washed with water (2×100 ml) and brine (100 ml) before drying (Na₂SO₄) and evaporating to a crude foam. Dissolution in ethyl acetate and treatment with hexane then ether, gave the purified title compound as a white solid (115 mg, 25%), m.p. 162°–164° (dec).

T.l.c. SiO₂, ethyl acetate, Rf 0.71.

EXAMPLE 35

Dihydro-1-[3-(4-Methoxyphenyl)phenyl]-1,2,4-triazine-3,5-(2H,4H)-dione

(a) 3-[4-methoxy(phenylmethoxy)]nitrobenzene (Intermediate 86)

A mixture of 3-nitrophenol (18.49 g, 0.133 mol), anhydrous potassium carbonate (19.2 g, 0.139 mol), potassium iodide (21.0 g, 0.127 mol) and 4-methoxybenzyl chloride (19.82 g, 0.127 mol) in acetone (200 ml) was heated under reflux for 48 h.

The inorganic material was filtered off and the solvent evaporated in vacuo to an orange solid residue. Recrystallisation from ethanol gave the title compound; (Intermeidate 86) as a pale yellow crystalline solid (29.6 g; 89.9%), m.p. 82°-84°.

T.l.c. $SiO_2$ ethyl acetate, Rf 0.76.

(b) 3-[4-Methoxy(phenylmethoxy)]benzenamine (Intermediate 87)

The nitrobenzene (Intermediate 86, 5 g, 19.3 mmol) was hydrogenated at atmospheric pressure over 5% platinum oxide on carbon (0.2 g) in methanol (50 ml) and dioxane (100 ml) for 0.25 h.

The catalyst was removed by filtration through hyflo and the solvent evaporated to leave the title compound (Intermediate 87) as a white solid (4.1 g; 93%), m.p. 105°-107°.

T.l.c. $SiO_2$ ethyl acetate, Rf 0.65.

(c) N-[3-(4-Methoxyphenylmethoxy)phenyl]glycine, methyl ester (Intermediate 88)

A mixture of the aniline (Intermediate 87, 24.6 g, 107.3 mmol), sodium bicarbonate (13.5 g, 161 mmol) and methyl chloracetate (10.1 ml, 118 mmol) in acetonitrile (30 ml) was heated at 90°-100° for 48 h. Water (200 ml) was added and the mixture extracted with ethyl acetate (3×100 ml). The combined extracts were washed with water (2×100 ml) and brine (100 ml) before drying ($Na_2SO_4$) and evaporating in vacuo to leave the crude product as a peach solid. Trituration with ether-hexane (1:1) gave the title compound (Intermediate 88) as a flesh coloured solid (30.3 g; 94%), m.p. 79°-81°.

T.l.c. $SiO_2$, ethyl acetate, RF 0.67.

(d) Methyl 1-[3-[4-methoxyphenylmethoxy]phenyl]hydrazino acetate (Intermediate 89)

Sodium nitrite (7.51 g, 109 mmol) in water (80 ml) was added at 0°-5° to a stirred solution of the glycine (Intermediate 88, 29.9 g, 99 mmol) in glacial acetic acid (300 ml) and methanol (80 ml). The deep orange-brown solution was stirred at <0° C. for 2 h. Zinc dust (22.65 g; 347 mmol) was added over 0.5 h at ≦0° and the resulting suspension stirred at ≦0° for 3 h. The zinc residues were filtered through hylfo and the filtrate diluted with water (500 ml) and extracted with ethyl acetate (3×100 ml). The combined extracts were washed with 8% sodium bicarbonate (4×500 ml), water (2×500 ml) and brine (500 ml) before drying ($Na_2SO_4$) and evaporating in vacuo to leave the crude hydrazine as a brown oil (19.1 g). Column chromatography on solica (Merck 9385 500 g) eluting with hexane/ether (1:1) gave the title compound (Intermediate 89) as a white solid (4.4 g; 13.7%), m.p. 85°-87°.

T.l.c. $SiO_2$, ether Rf 0.34.

(e) Methyl[2-AMinocarbonyl)-1-[3-[4-methoxyphenylmethoxy]phenyl]hydrazino]acetate (Intermediate 90)

Sodium cyanate (0.21 g, 3.16 mmol) in water (10 ml) was added dropwise to a solution of the hydrazino (Intermediate 89), 500 mg, 1.58 mmol) in water (10 ml) and acetic acid (10 ml) at 45° C. The reaction mixture was stirred at 40° C. for 15 minutes, then left stirring at room temperature for 3 hours. Water (25 ml) was then added and the mixture was extracted with ethyl acetate (2×25 ml). The combined extracts were washed with (8% sodium bicarbonate in vacuo to leave a brown solid (454 mg). Recrystallisation from ethyl acetate gave the title compound (Intermediate 90) as a beige coloured solid (140 mg, 25%). Concentration of the mother liquid gave a further crude sample of the title compound (290 mg 51%).

T.l.c. $SiO_2$, ethyl acetate. Rf=0.25.
m.p. 136°-138° C.

(f) Dihydro-1-[3-[4-methoxyphenylmethoxy]phenyl]-1,2,4-triazine-3,5 (2H,4H)-dione Potassium t-butoxide was added to a stirred suspension of the urea (Intermediate 90, 960 mg, 2.7 mmol) in dimethoxyethane and the mixture was stirred at room temperatures for 30 minutes. The mixture was then poured into pH6.5 aqueous phosphate buffer (100 ml) and extracted with ethyl acetate (3×50 ml). The combined extracts were washed with water (50 ml), brine (50 ml), dried ($Na_2SO_4$) and evaporated to leave the crude product (750 mg) as a brown solid. This was recrystallised from dichloromethane to give a cement coloured solid (250 mg). Finally, it was treated with decolourising charcoal and then recrystallised from ethanol to give a white solid, m.p. 170°-176° (dec).

T.l.c. $SiO_2$, Ethyl Acetate, Rf 0.67.

EXAMPLE 36

Dihydro-1-[3-(methylphenyl)-1,2,4-triazine-3,5-(2H,4H)-dione

(a) [2-Aminocarbonyl)-1-(3-methylphenyl)hydrazino]acetic acid (Intermediate 91)

2N Sodium hydroxide (25 ml) was added to a stirred suspension of methyl [2-(aminocarbonyl)-1-[3-methylphenyl)hydrazino]acetate (prepared as described in Example 1) (3 g, 12.6 mmol) in methanol (30 ml), and the solution was stirred at 25° for 18 h. The mixture was then poured into 2N hydrochloric acid (100 ml) and extracted with ethyl acetate (2×100 ml). The extracts were dried ($Na_2SO_4$) and evaporated to a white solid residue which upon trituration with diethyl ether (50 ml) gave a white solid (1.75 g; 62%), mp. 194°-196°.

T.l.c. $SiO_2$, Ethyl Acetate, Rf 0.23.

(b) Dihydro-1-[3-methylphenyl)]-1,2,4-triazine-3,5-(2H,4H)-dione

Diphenylphosphoryl azide (0.6 ml, 2.8 mmol) was added at 20°-25° to a stirred solution of the acid (Intermediate 91, 250 mg, 1.12 mmol) in dichloromethane (25 ml) containing triethylamine (0.39 ml, 2.8 mmol). The mixture was stirred at 20°-25° overnight during which time a fine precipitate was formed. pH6.7 buffer (50 ml) was added and the mixture was extracted with ethyl acetate (3×50 ml). The combined extracts were washed with water (2×100 ml) and brine (100 ml) before drying (Na₂SO₄) and evaporating in vacuo to a yellowish semi-solid. Trituration with ether gave a white solid (202 mg; 88%), m.p. 250°–254°.

T.l.c., SiO₂, Ethyl Acetate, Rf 0.67.

EXAMPLE 37

Dihydro-1-(3-hexyl phenyl)-1,2,4-triazine-3,5-(2H,4H)-dione (a)

Methyl[2-(aminocarbonyl]-1-[3-[(hex-1-yne)phenyl]hydrazino]acetate (Intermediate 92)

Methyl[2-(aminocarbonyl)-1-(3-iodophenyl)hydrazino]acetate (Intermediate 29, 1 g, 2.9 mmol)hexyne (0.362 ml, 3.2 mmol) cuprous iodide (3 mg, 0.5%), bis(triphenylphosphine)palladium (II) chloride (20 mg, 1%) and N-N-diisopropylethylamine (0.748 ml; 4.3 mmol) were allowed to stir under nitrogen, in THF (10 ml) for 3 days. A further amount of hexyne (0.362 ml), CuI (3 mg), Pd(PPh₃)₂Cl₂ (20 mg) and N,N-diisopropylethylamine (0.748 ml) were added. The mixture was left for 24 hr. The THF was evaporated and the reaction was quenched with ammonium chloride. It was extracted with ether and the ether extracts were washed with water and brine and then dried (Na₂SO₄). Filtration and evaporation followed by chromatography in 3% MeOH/CH₂Cl₂ gave Intermediate 92 (700 mg, 80%) as a glassy solid.

T.l.c., SiO₂ 10% methanol in Dichloromethane, Rf 0.58.

(b) Methyl [2-aminocarbonyl]-1-[3-hexylphenyl]hydrazino]acetate (Intermediate 93)

The urea (Intermediate 92, 630 mg, 2 mmol) and catalyst (5% Pd/C, 65 mg) in a solution of the THF/methanol (9:1) were stirred in a hydrogen atmosphere for 3 hours. The catalyst was filtered through celite and the filtrate evaporated to give a crude product. This was triturated with ether to yield the title compound (Intermediate 93, 603 mg, 95%) as a white solid, m.p. 95°–99°.

(c)

Dihydro-1-(3-hexylphenyl)-1,2,4-triazine-3,5(2H,4H) dione

Sodium methoxide (105 mg; 2.0 mmol) was added to a stirred solution of the urea (Intermediate 93, 300 mg-1.0 mmol) in DME (10 ml) over 4A molecular sieves. After 1 h, the reaction mixture was poured into pH 6.5 aqueous phosphate buffer (30 ml) and extracted with EtOAc. The extracts were washed (water, brine) and dried (Na₂SO₄) before evaporating to give a crude product. This was triturated with ether and left to cool overnight to give the title compound (59 mg; 24%) as an impure solid. A second solid (67 mg- 25%) was obtained from filtration of the water wash. The triturants of the first batch were evaporated and chromatographed with 50% Ether/hexane to give solid material (21 mg), m.p. 143°–145°.

T.l.c., SiO₂, Ethyl Acetate/Hexane, Rf 0.60.

EXAMPLE 38

Dihydro-1-(3-octylphenyl)-1,2,4-triazine-3,5-(2H,4H)-dione (a)

Methyl[2-aminocarbonyl]-1-[3-(oct-1-yne)phenyl]hydrazino]acetate (Intermediate 94)

Methyl[2-(aminocarbonyl)-1-[3-iodophenyl)hydrazino]acetate (Intermediate 29, 1 g, 2.9 mmol), octyne (0.465 ml, 3.3 mmol), cuprous iodide (3 mg, 0.5%), bis(triphenylphosphine)palladium(II) chloride (20 mg, 1%) and N-N-diisopropylethylamine (0.74 ml, 43 mmol) were allowed to stir, under nitrogen, in THF (10 ml) for 3 days. Further amounts of octyne (0.465 ml), CuI (3 mg), Pd(PPh₃)₂Cl₂ (20 mg) and N,N-diisopropylethylamine (0.748 ml, 43 mmol) were added. The mixture was left for 24 h. The THF was evaporated and the reaction quenched with ammonium chloride. It was extracted with ether and the extracts were washed with water and brine and then dried (Na₂SO₄). Filtration and evaporation followed by chromatography in 3% MeOH/CH₂Cl₂ gave Intermediate 94 (700 mg, 74%) as a glassy solid. On trituration with hexane an off white solid was obtained (650 mg, 68%) m.p. 86°–89°.

T.l.c., SiO₂, 10% Methanol in Dichloromethane, Rf 0.58.

(b) Methyl [2-(aminocarbonyl]-1-[3-(octylphenyl)]hydrazino]acetate (Intermediate 95)

The octyne (Intermediate 94, 1 g, 3 mmol) was dissolved in THF/methanol (9:1) mixture. Palladium on carbon (5%, 100 mg) was added under nitrogen and the reaction was allowed to stir in a hydrogen atmosphere for 4 h. The excess catalyst was removed by filtration through celite. The filtrate was evaporated to yield an oil. Trituration with ether/hexane (1:1) and cooling yielded Intermediate 95 (837 mg, 86%) as a white solid, m.p. 92°–93°.

(c)

Dihydro-1-(3-octylphenyl)-1,2,4-triazine-3,5-(2H,4H)dione

The urea (Intermediate 95, 300 mg; 0.9 mmol) was stirred in DME (7 ml) over 4A molecular sieves. Sodium methoxide was added (112 mg; 2 mmol) and the reaction was left to stir for 2 h under nitrogen. The reaction mixture was poured into pH 6.5 aqueous phosphate buffer (20 ml) and extracted (ethyl acetate). The organic extracts were washed (water, brine) and dried (Na₂SO₄). Evaporation and trituration (ether/hexane) gave a triturant from which was obtained the title compound (77 mg, 28%) as a solid, m.p. 169°–171°.

T.l.c., SiO₂, Ethyl Acetate/Hexane (3:1), Rf 0.54.

EXAMPLE 39

Dihydro-1-[4-methoxy-3-methylphenyl]-1,2,4-triazine-3,5-(2H,4H)-dione (a) N-(4-Methoxy-3-methylphenyl)glycine, methyl ester (Intermediate 96)

A mixture of 4-methoxy-3-methylaniline (5 g, 0.0364 mol), methyl glyoxylate (5.5 g, 0.0619 mol) and palladium over charcoal (3.7 g; 10%) in methanol (300 ml) was stirred under a hydrogen atmosphere for 1 hour. The suspension was filtered through hyflo and evaporated to give a yellow solid. This was triturated with ether at ~ −78° C. and filtered to give the title compound as a pale yellow solid (3.8 g, 50%) m.p. 69°–71° C.

T.l.c. SiO$_2$, Ether/hexane 1:1, Rf 0.5.

(b) Methyl [1-[4-methoxy-3-methylphenyl]hydrazino]acetate (Intermediate 97)

N-(4-methoxy-3-methylphenyl)glycine, methyl ester (Intermediate 96, 5 g, 0.0239 mol) was dissolved in a mixture of glacial acetic acid (45 ml) and water (3 ml) and the solution was cooled to ~5° C. To this was added a solution of sodium nitrite (1.7 g, 0.0251 mol) in water (5 ml) over 30 minutes and the reaction was stirred for one hour. Zinc dust (6 g, 0.093 mol) was added over 1½ hours at the same low temperature and stirred at room temperature for 1 hour. The reaction was poured into water (150 ml) and extracted with ethyl acetate (2×100 ml). The organic extract was washed with 8% sodium bicarbonate solution until effervescence had ceased, then dried (MgSO$_4$) and evaporated to give a yellow oil. This was purified by flash column chromatography on silica (Merck 9385; 100 g) eluting with ether-hexane 1:1 to give the title compound as an orange oil (0.4 g, 7%).

T.l.c., SiO$_2$ Ether/hexane (1:1), Rf 0.15.

(c) Methyl [2-[aminocarbonyl]-1-[4-methoxy-3-methylphenyl]hydrazino]acetate (Intermediate 98)

A mixture of methyl [1-[4-methoxy-3-methylphenyl]-hydrazino]acetate (Intermediate 97, 380 mg, 0.0017 mol), sodium cyanate (380 mg, 0.0058 mol) and trifluoroacetic acid (0.4 ml, 0.0052 mol) in dry toluene (10 ml) was stirred under nitrogen and at room temperature for 3½ hours. It was poured into 8% sodium bicarbonate solution (20 ml) and extracted with ethyl acetate (2×20 ml). The organic extract was dried (MgSO$_4$) and evaporated to give a yellow solid which was triturated with ether and filtered to give the title compound as a yellow solid (237 mg, 52%) m.p. 174°–176° C.

T.l.c., SiO$_2$, Ethyl Acetate Rf 0.36.

(d) Dihydro-1-[4-methoxy-3-methylphenyl]-1,2,4-triazine-3,5-(2H,4H)-dione

To a solution of methyl [2-[aminocarbonyl]-1-[4-methoxy-3-methyl phenyl]hydrazino]acetate (Intermediate 98, 222 mg, 0.8 mmol) in methanol (5 ml) was added sodium methoxide (43 mg, 0.8 mmol) with stirring and under nitrogen. After 30 minutes further sodium methoxide (43 mg, 0.8 mmol) was added and the reaction stirred at room temperature for 14 hours. Three separate portions of sodium methoxide (43 mg, 0.8 mmol) were then added with 30 minutes between each before the reaction was poured into pH 6 buffer (30 ml) and extracted with ethyl acetate (2×25 ml). The organic extract was dried (MgSO$_4$) and evaporated to give a white semi-solid which was triturated with ethylacetate-ether (~1:1) to give an off white solid. This was dissolved in ethyl acetate (10 ml), filtered and evaporated to give the title compound as an off white solid (18 mg, 10%) m.p. 220°–222° C. (decomp).

T.l.c., SiO$_2$ Ethyl Acetate, Rf 0.82.

The following examples illustrate pharmaceutical formulations according to the invention. The term "active ingredient" is used herein to represent a compound of formula (I).

PHARMACEUTICAL EXAMPLE 1

| Oral Tablet A | |
|---|---|
| Active Ingredient | 700 mg |
| Sodium starch glycollate | 10 mg |
| Microcrystalline cellulose | 50 mg |
| Magnesium Stearate | 4 mg |

Sieve the active ingredient and microcrystalline cellulose through a 40 mesh screen and blend in a appropriate blender. Sieve the sodium starch glycollate and magnesium stearate through a 60 mesh screen, add to the powder blend and blend until homogeneous. Compress with appropriate punches in an automatic tablet press. The tablets may be coated with a thin polymer coat applied by the film coating techniques well known to those skilled in the art. Pigments may be incorporated in the film coat.

PHARMACEUTICAL EXAMPLE 2

| Oral Tablet B | |
|---|---|
| Active Ingredient | 500 mg |
| Lactose | 100 mg |
| Maize Starch | 50 mg |
| Polyvinyl pyrrolidone | 3 mg |
| Sodium Starch glycollate | 10 mg |
| Magnesium stearate | 4 mg |
| Tablet Weight | 667 mg |

Sieve the active ingredient, lactose and maize starch through a 40 mesh screen and blend the powders in a suitable blender. Make an aqueous solution of the polyvinyl pyrrolidone (5–10% w/v). Add this solution to the blended powders and mix until granulated; pass the granulate through a 12 mesh screen and dry the granules in a suitable oven or fluid bed dryer. Sieve the remaining components through a 60 mesh screen and blend them with dried granules. Compress, using appropriate punches on an automatic tablet press.

The tablet may be coated with a thin polymer coat applied by film coating techniques well known to those skilled in art. Pigments may be incorporated in the film coat.

PHARMACEUTICAL EXAMPLE 3

| Inhalation Cartridge | |
|---|---|
| Active Ingredient | 1 mg |
| Lactose | 24 mg |

Blend active ingredient, particle size reduced to a very fine particle size (weight mean diameter ca. 5 μm) with the lactose in a suitable powder blender and fill the powder blender into No. 3 hard gelatin capsules.

The contents of the cartridges may be administered using a powder inhaler.

What is claimed is:

1. A triazine derivative of formula (I)

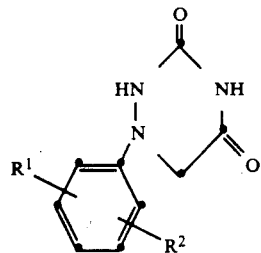

(I)

or a salt thereof, wherein $R^1$ represents a halogen atom or a group selected from hydroxy; $C_{1-8}$ alkyl; $C_{1-6}$ alkoxy; $C_{1-3}$ alkoxy $C_{1-3}$ alkoxy; phenoxy or phenyl $C_{1-3}$ alkoxy, wherein the phenyl group is optionally substituted by a halogen atom or a group selected from $C_{1-3}$ alkyl, $C_{1-3}$ alkoxy, and hydroxy; fluoro $C_{1-3}$ alkyl; cyano; —$CO_2R^3$, wherein $R^3$ represents a hydrogen atom or a $C_{1-4}$ alkyl group; and —$CONR^4R^5$, wherein $R^4$ and $R^5$ each independently represents a hydrogen atom or a $C_{1-4}$ alkyl group; and $R^2$ represents a hydrogen or halogen atom, or a group selected from hydroxy, $C_{1-6}$ alkyl and $C_{1-6}$ alkoxy.

2. A triazine derivative according to claim 1 wherein $R^1$ represents a halogen atom or a group selected from $C_{1-8}$ alkyl; $C_{1-6}$ alkoxy; $C_{1-3}$ alkoxy $C_{1-3}$ alkoxy; phenoxy and phenyl $C_{1-3}$ alkoxy, wherein the phenyl group is optionally substituted by a halogen atom or a group selected from $C_{1-3}$ alkyl, $C_{1-3}$ alkoxy and hydroxy; and fluoro $C_{1-3}$ alkyl; and $R^2$ is as defined in claim 1; or a physiologically acceptable salt thereof.

3. A triazine derivative according to claim 1 wherein $R^1$ represents a a phenyl $C_{1-3}$ alkoxy group.

4. A triazine derivative according to claim 1 wherein $R^1$ represents a trifluoromethyl group.

5. A triazine derivative according to claim 1 wherein $R^1$ represents a halogen atom and $R^2$ is as defined in claim 1; or a physiologically acceptable salt thereof.

6. A triazine derivative according to claim 5 wherein $R^1$ represents a fluorine atom.

7. A triazine derivative according to claim 1 wherein $R^1$ represents a $C_{1-8}$ alkyl group, and $R^2$ is as defined in claim 1; or a physiologically acceptable salt thereof.

8. A triazine derivative according to claim 7 wherein $R^1$ represents a $C_{1-3}$ alkyl group.

9. A triazine derivative according to claim 8 wherein $R^1$ represents a methyl or an ethyl group.

10. A triazine derivative according to claim 9 wherein $R^1$ represents a methyl group.

11. A triazine derivative according to claim 1 wherein $R^2$ represents a hydrogen or halogen atom, or a $C_{1-6}$ alkyl group.

12. A triazine derivative according to claim 11 wherein $R^2$ represents a hydrogen atom.

13. A triazine derivative according to claim 11 wherein $R^2$ represents a halogen atom.

14. A triazine derivative according to claim 13 wherein $R^2$ represents a fluorine atom.

15. A triazine derivative according to claim 11 wherein $R^2$ represents a $C_{1-6}$ alkyl group.

16. A triazine derivative according to claim 15 wherein $R^2$ represents a methyl group.

17. A triazine derivative according to claim 1 wherein $R^1$ is a 3- or 4- phenyl substituent.

18. dihydro-1-(3-fluorophenyl)-1,2,4-triazine-3,5-(2H,4H)-dione; or a physiologically acceptable salt thereof.

19. Dihydro-1-(3-methylphenyl)-1,2,4-triazine-3,5-(2H,4H)-dione; or a physiologically acceptable salt thereof.

20. Dihydro-1-(3-ethylphenyl)-1,2,4-triazine-3,5-(2H,4H)-dione; or a physiologically acceptable salt thereof;

Dihydro-1-(3-n-propylphenyl)-,1,2,4-triazine-3,5-(2H,4H)-dione; or a physiologically acceptable salt thereof;

Dihydro-1-(4-fluorophenyl)-,1,2,4-triazine-3,5-(2H,4H)-dione; or a physiologically acceptable salt thereof;

Dihydro-1-(3-chlorophenyl)-,1,2,4-triazine-3,5-(2H,4H)-dione; or a physiologically acceptable salt thereof;

Dihydro-1-(3-bromophenyl)-,1,2,4-triazine-3,5-(2H,4H)-dione; or a physiologically acceptable salt thereof;

Dihydro-1-(3,5-difluorophenyl)-,1,2,4-triazine-3,5-(2H,4H)-dione; or a physiologically acceptable salt thereof.

21. A method of treatment for the relief or prevention of diseases in which leukotrienes and other 5-lipoxygenase products are mediators which comprises administering, to a human or animal subject in need of such treatment, an effective amount of a triazine derivative according to claim 1 or a physiologically acceptable salt thereof.

22. A pharmaceutical composition comprising a triazine derivative according to claim 1 or a physiologically acceptable salt thereof in association with a physiologically acceptable carrier or excipient.

* * * * *